(12) United States Patent
Shen et al.

(10) Patent No.: US 7,973,146 B2
(45) Date of Patent: Jul. 5, 2011

(54) ENGINEERED FLUORESCENT DYE LABELED NUCLEOTIDE ANALOGS FOR DNA SEQUENCING

(75) Inventors: Gene Shen, Santa Clara, CA (US); Paul Peluso, San Carlos, CA (US); Arkadusz Bibillo, Cupertino, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 44 days.

(21) Appl. No.: 12/412,068

(22) Filed: Mar. 26, 2009

(65) Prior Publication Data

US 2009/0246791 A1 Oct. 1, 2009

Related U.S. Application Data

(60) Provisional application No. 61/070,823, filed on Mar. 26, 2008.

(51) Int. Cl.
*C07G 3/00* (2006.01)
*C07H 21/04* (2006.01)
*C12Q 1/68* (2006.01)
*C12P 19/34* (2006.01)

(52) U.S. Cl. .......... 536/4.1; 536/24.3; 536/24.33; 536/26.6; 435/6; 435/91.1; 435/91.2

(58) Field of Classification Search ........... 536/4.1, 536/26.6, 24.3, 24.33; 435/6, 91.1, 91.2
See application file for complete search history.

(56) References Cited

U.S. PATENT DOCUMENTS

| | | | |
|---|---|---|---|
| 5,688,648 A | 11/1997 | Mathies et al. | |
| 6,056,661 A | 5/2000 | Schmidt | |
| 6,232,075 B1 | 5/2001 | Williams | |
| 6,255,083 B1 | 7/2001 | Williams | |
| 6,699,723 B1 | 3/2004 | Weiss et al. | |
| 6,762,048 B2 | 7/2004 | Williams | |
| 6,861,155 B2 | 3/2005 | Bawendi et al. | |
| 6,917,726 B2 | 7/2005 | Levene et al. | |
| 7,033,764 B2 | 5/2006 | Korlach et al. | |
| 7,052,839 B2 | 5/2006 | Nelson et al. | |
| 7,052,847 B2 | 5/2006 | Korlach et al. | |
| 7,056,676 B2 | 6/2006 | Korlach et al. | |
| 7,170,050 B2 | 1/2007 | Turner et al. | |
| 7,223,541 B2 | 5/2007 | Fuller et al. | |
| 7,229,799 B2 | 6/2007 | Williams | |
| 7,235,361 B2 | 6/2007 | Bawendi et al. | |

(Continued)

FOREIGN PATENT DOCUMENTS

WO WO2007/075873 7/2007

(Continued)

OTHER PUBLICATIONS

Benjamin Schuler, et al., "Polyproline and the "spectroscopic ruler" revisited with single-molecule fluorescence", PNAS, Feb. 22, 2005; vol. 102, No. 8; 2754-2759.

(Continued)

*Primary Examiner* — Jezia Riley
(74) *Attorney, Agent, or Firm* — Matthew B. Murphy

(57) ABSTRACT

Engineered nucleotide compositions, having polymerase interacting components that improve the interactivity of the polymerase and the nucleotide, particularly for nucleic acid sequencing applications. Compositions include the interactive polymerases along with the nucleotide analogs. Kits, methods and systems are provided for analysis of nucleic acid synthesis reactions.

10 Claims, 13 Drawing Sheets

U.S. PATENT DOCUMENTS

| | | |
|---|---|---|
| 2003/0124576 A1 | 7/2003 | Kumar et al. |
| 2007/0036511 A1 | 2/2007 | Lundquist et al. |
| 2007/0072196 A1 | 3/2007 | Xu et al. |
| 2007/0128133 A1 | 6/2007 | Eid et al. |
| 2007/0161017 A1 | 7/2007 | Eid et al. |
| 2007/0188750 A1 | 8/2007 | Lundquist et al. |
| 2007/0196846 A1 | 8/2007 | Hanzel et al. |
| 2008/0277595 A1 | 11/2008 | Lundquist et al. |
| 2009/0024331 A1 | 1/2009 | Tomaney et al. |
| 2009/0186343 A1* | 7/2009 | Wang et al. .............. 435/6 |

FOREIGN PATENT DOCUMENTS

| | | |
|---|---|---|
| WO | WO2007/075987 | 7/2007 |
| WO | WO2007/076057 | 7/2007 |
| WO | WO2007/095119 | 8/2007 |

OTHER PUBLICATIONS

Inoue, T. et al., "Synthesis and evaluation of 1-position-modified inositol 1,4,5-trisphosphate analogs" Bioorg & Medicinal Chem Lett (1999) 9:1697-1702.

Nakanishi, W. et al., "Hydrophobic modifications at 1-phosphate of inositol 1,4,5-trisphosphate analogues enhance receptor binding" Bioorg & Medicinal Chem Lett (2002) 12:911-913.

Yogo, T. et al., "Selective photoinactivation of protein functioin through environment-sensitive switching of singlet oxygen generation by photosensitizer" PNAS (2008)105(1):28-32.

* cited by examiner

```
                        1                                                                                                  100
B103    (1)  -MPRKMFSCDFETTTKLDDCRVWAYGYMEIGNLDNYKIGNSLDEFMQWVMEIQADLYFHNLKFDGAFIVNWLEHHGFKWSNEG—LPNTYNTIISKM
M2      (1)  -MSRKMFSCDFETTTKLDDCRVWAYGYMEIGNLDNYKIGNSLDEFMQWVMEIQADLYFHNLKFDGAFIVNWLEQHGFKWSNEG—LPNTYNTIISKM
GA1     (1)  -MARSVYYCDFETTTDPEDCRLWAWGWMDIYNTDKWSYGEDIDSFMEWALNSNSDIYFHNLKFDGSFILPWWLRNGVHTEEDRTNTPKEFTTISGM
Phi29   (1)  MKHMPRKMYSCDFETTTKVEDCRVWAYGYMNIEDHSEYKIGNSLDEFMAWWLKVQADLYFHNLKFDGAFIINWLERNGFKWSADG—LPNTYNTIISRM
PZA     (1)  -MPRKMYSCDFETTTKVEDCRVWAYGYMNIEDHSEYKIGNSLDEFMAWWLKVQADLYFHNLKFDGAFIINWLERNGFKWSADG—LPNTYNTIISRM
                        101                                                                                                200
B103    (95) GQWYMIDICFGYKGKRKLHTVIYDSLKKLPFPVKKIAKDFQLPLLKGDIDYHAERPVGHEITPEEYEYIKNDIEIIARALDIQFKQGLDRMTAGSDSLKG
M2      (95) GQWYMIDICFGYKGKRKLHTVIYDSLKKLPFPVKKIAKDFQLPLLKGDIDYHTERPVGHEITPEEYEYIKNDIEIIARALDIQFKQGLDRMTAGSDSLKG
GA1     (98) GQWYAVDVCINTRGKNKNHVFYDSLKKLPFKVEQIAKGFGLPVLKGDIDYKKYRPVGYVMDDNEIEYLKHDLLIVALALRSMFDNDFTSMTVGSDALNT
Phi29   (98) GQWYMIDICLGYKGKRKIHTVIYDSLKKLPFPVKKIAKDFKLTVLKGDIDYHKERPVGYKITPEEYAYIKNDIQIIAEALLIQFKQGLDRMTAGSDSLKG
PZA     (95) GQWYMIDICLGYKGKRKIHTVIYDSLKKLPFPVKKIAKDFKLTVLKGDIDYHKERPVGYEITPDEYAYIKNDIQIIAEALLIQFKQGLDRMTAGSDDLKG
                        201                                                                                                300
B103    (195) FKDILSTKKFNKVFPKLSLPMDKEIRRAYRGGFTWLNDKYKEKEIGEGMVFDVNSLYPSQMYSRPLPYGAPIVFQGKYEKDEQYPLYIQRIRFEFELKEG
M2      (195) FKDILSTKKFNKVFPKLSLPMDKEIRKAYRGGFTWLNDKYKEKEIGEGMVFDVNSLYPSQMYSRPLPYGAPIVFQGKYEKDEQYPLYIQRIRFEFELKEG
GA1     (198) YKEMLGVKQWEKYFPVLSLKVNSEIRKAYKGGFTWVNPKYQGETVYGGMVFDVNSMYPAMMKNKLLPYGEPVMFKGEYKKNVEYPLYIQQVRCFFELKKD
Phi29   (198) FKDIITTKKFKKVFPTLSLGLDKEVRYAYRGGFTWLNDRFKEKEIGEGMVFDVNSLYPAQMYSRLLPYGEPIVFEGKYVWDEDYPLHIQHIRCEFELKEG
PZA     (195) FKDIITTKKFKKVFPTLSLGLDKEVRYAYRGGFTWLNDRFKEKEIGEGMVFDVNSLYPAQMYSRLLPYGEPIVFEGKYVWDEDYPLHIQHIRCEFELKEG
                        301                            375↓                                                               400
B103    (295) YIPTIQIKKNPFFKGNEYLKNSGAEPVELYLTNVDLELIQEHYEMYNVEYIDGFKFREKTGLFKFEFIDKWTYVKTHEKGAKKQ-LAKLMFDSLYGKFAS
M2      (295) YIPTIQIKKNPFFKGNEYLKNSGVEPVELYLTNVDLELIQEHYELYNVEYIDGFKFREKTGLFKFEFIDKWTYVKTHEEGAKKQ-LAKLMLNSLYGKFAS
GA1     (298) KIPCIQIKGNARFGQNEYLSTSGDEYVDLYVTNVDWELIKKHYDIFEEEFIGGFMFKGFIGFFEYIDRFMEIKNSPDSSAEQSLQAKLMLNSLYGKFAT
Phi29   (298) YIPTIQIKKRSRFYKGNEYLKSSGGEIADLWLSNVDLENMKEHYDLYNVEYISGLKFKATTGLFKFDIDKWTYIKTTSEGAIKQ-LAKLMLNSLYGKFAS
PZA     (295) YIPTIQIKKRSRFYKGNEYLKSSGGEIADLWVSNVDLELMKEHYDLYNVEYISGLKFKATTGLFKFDIDKWTHIKTTSEGAIKQ-LAKLMLNSLYGKFAS
                        401                                                                                                500
B103    (393) NPDVTGKVPYLKEDGSLGFRVGDEEYKDPVYTPMGVFITAAQACYDRIIYCDTDSIHLTGTEVPEIIKDIVDPKKLGYWAHESTFKRAKYL
M2      (393) NPDVTGKVPYLKDDGSLGFRVGDEEYKDPVYTPMGVFITAWARFTTITAAQACYDRIIYCDTDSIHLTGTEVPEIIKDIVDPKKLGYWAHESTFKRAKYL
GA1     (398) NPDITGKVPYLKFRKGELKERDPVYTPMGCFITAYARENILSNAQKLYPRFIYADTDSIHVEGLGEVDAIKDVIDPKKLGYWDHEATFQRARYV
Phi29   (396) NPDVTGKVPYLKENGALGFRLGEEETKDPVYTPMGVFITAWARYTTITAAQACYDRIIYCDTDSIHLTGTEIPDVIKDIVDPKKLGYWAHESTFKRAKYL
PZA     (393) NPDVTGKVPYLKENGALGFRLGEEETKDPVYTPMGVFITAWARYTTITAAQACFDRIIYCDTDSIHLTGTEIPDVIKDIVDPKKLGYWAHESTFKRAKYL
                        501     512↓                                  581
B103    (493) RQKTYIQDIYAKEVDG-KLIECSPDEATTTKFSVKCAGMTDTIKKKVTFDNFRVGFSSTGKPKPVQVNGGVVLVDSVFTIK
M2      (493) RQKTYIQDIYVKEVDG-KLKECSPDEATTTKFSVKCAGMTDTIKKKVTFDNFAVGFSSMGKPKPVQVNGGVVLVDSVFTIK
GA1     (498) RQKTYFIETTWKENDKGKLVCEPQDATKVKPKIACAGMSDAIKERIRFNEFKIGYSTHGSLKPKNVLGGVVLMDYPFAIK
Phi29   (496) RQKTYIQDIYMKEVDG-KLVEGSPDDYTIKFSVKCAGMTDKIKKEVTFENFKVGFSRKMKPKPVQVPGGVVLVDDTFTIK
PZA     (493) RQKTYIQDIYMKEVDG-KLVEGSPDDYTTIKFSVKCAGMTDKIKKEVTFENFKVGFSRKMKPKPVQVPGGVVLVDDTFTIK
```

Figure 4

ENGINEERED FLUORESCENT DYE LABELED NUCLEOTIDE ANALOGS FOR DNA SEQUENCING

CROSS-REFERENCE TO RELATED APPLICATIONS

This application claims benefit of Provisional U.S. Patent Application No. 61/070,823, filed Mar. 26, 2008, the full disclosure of which is hereby incorporated herein by reference in its entirety for all purposes.

STATEMENT REGARDING FEDERALLY SPONSORED RESEARCH

Not Applicable.

BACKGROUND OF THE INVENTION

Genetic analysis is a fundamental tool in life sciences research, including, for example, pharmaceutical development, medical diagnostics, agriculture, and academic research toward understanding the basic operation of life. A large number of tools have been developed to facilitate such genetic analysis and manipulation, including, for example, nucleic acid amplification and monitoring techniques, nucleic acid sequencing techniques, and expression profiling techniques.

Despite major advances in each of these areas over the past several decades, there always remains room for improvement of even the state of the art techniques. By way of example, recent advances in nucleic acid sequencing employ optical confinement techniques to provide the ability to eavesdrop on polymerase enzymes as they incorporate labeled nucleotide analogs in a template mediated primer extension reaction, providing a real-time monitoring of nucleic acid synthesis that is exploited to identify the sequence of nucleotides in the template nucleic acid. The technique is used for the full range of genetic analysis, including site specific sequencing, genotype analysis, re-sequencing, and de novo sequencing applications.

The ability to observe the real time synthesis of nucleic acids and so derive their sequences pushes the horizons of genetic analysis further back to expose other potential opportunities for improvements to genetic analysis technology. The present invention identifies some of these opportunities and provides a number of solutions.

BRIEF SUMMARY OF THE INVENTION

The present invention is generally directed to nucleotide analogs, and preferably labeled nucleotide analogs that serve as substrates for nucleic acid polymerase enzymes. The nucleotide analogs of the invention are generally characterized by having a polymerase interacting component engineered into their structure, which polymerase interacting component enhances the interaction between the polymerase and the analog. In particularly preferred aspects, the polymerase interacting component is positioned within a linking component that links the nucleotide portion of the analog with the labeling portion of the analog, and is situated as to be in interactive proximity to one or more amino acid residues of the polymerase enzyme, e.g., one or more residues in or near the catalytic center of the polymerase enzyme.

In a first aspect, the invention provides nucleotide compositions that comprise the structure:

N—Y—F wherein N is a nucleoside polyphosphate or analog thereof, F is a detectable label moiety, and Y comprises a polymerase interacting linkage complex. Optionally, the Y group comprises structures:

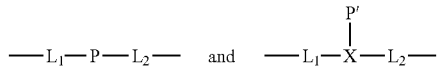

where $L_1$ is a first linker group, P or P' are a polymerase interacting group. $L_2$ is a second linker group, and X is a linking group.

In certain aspects, the compositions comprise the structures:

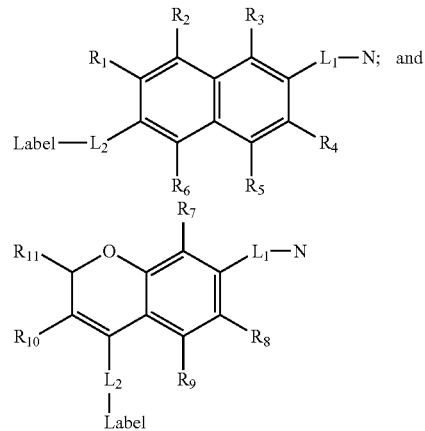

where $R_1$ through $R_{11}$ are independently selected from H, O, OH, positively charge groups and negatively charged groups.

In a related aspect, A nucleotide composition, comprising the structure:

N—Y—F where N is a nucleoside polyphosphate group or analog thereof coupled through a phosphate group other than an alpha phosphate group, L is a detectable labeling group, and Y comprises a polymerase interacting linkage complex having a polymerase interacting component selected from phenyl, biphenyl, triphenyl and a coumarin derivative.

In a further aspect, the invention provides nucleotide compositions, comprising the structure:

N-$L_1$-P-$L_2$-F wherein N is a nucleoside polyphosphate or analog thereof, $L_1$ is a first linker group, P is a polymerase interacting group, $L_2$ is a second linker group, and F is a detectable label moiety. In still other aspects, the invention provides methods of monitoring polymerase mediated, template dependent primer extension. Such methods comprise providing a polymerase template primer complex, contacting the complex with a nucleotide composition, comprising the structure:

N—Y—F wherein N is a nucleoside polyphosphate or analog thereof, F is a detectable label moiety, and Y comprises a polymerase interacting linkage complex, and monitoring reaction of the nucleotide composition with the complex in a primer extension reaction by detecting a signal from the detectable label.

BRIEF DESCRIPTION OF THE DRAWINGS

FIG. 4 provides a sequence alignment of a number of bacteriophage polymerases illustrating conserved structure within their active sites.

DETAILED DESCRIPTION OF THE INVENTION

I. General

Figure 1:
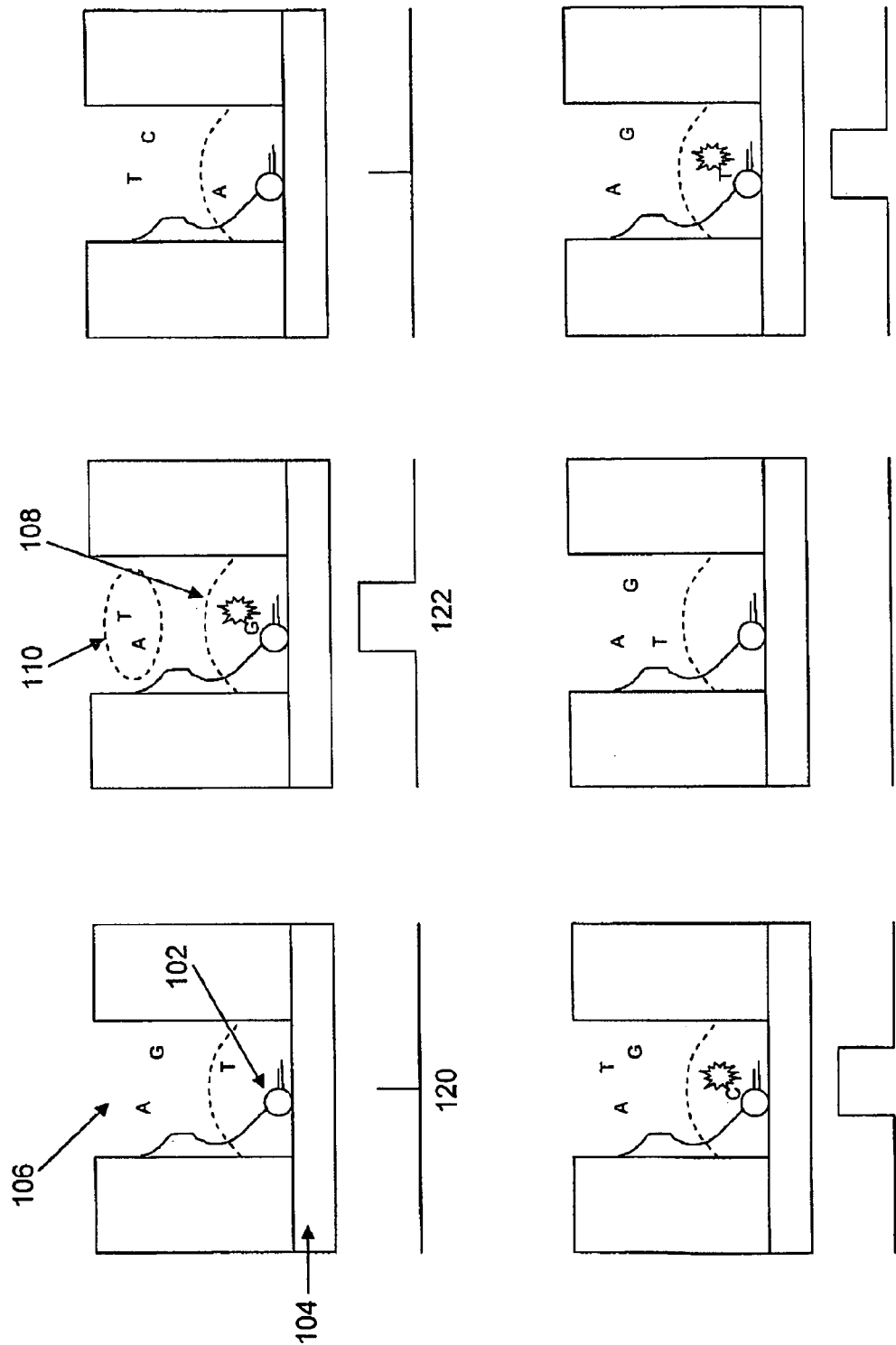
FIG. 1 provides a schematic illustration of a nucleic acid sequencing process.

The present invention is directed to novel compositions that are useful in nucleic acid synthesis reactions, and particularly such synthesis reactions exploited for the identification of sequence elements form nucleic acids. The compositions of the invention generally include novel nucleotides or nucleotide analogs, as well as combinations of such nucleotides or nucleotide analogs with nucleic acid polymerases that interact with and are capable of incorporating such nucleotides or nucleotide analogs in a template mediated primer extension reaction.

The nucleotide compositions of the invention are generally characterized by improved interactivity with a nucleic acid polymerase. In particular, the nucleotide compositions of the invention are typically engineered to provide one or more of improved reaction kinetics (e.g., Km, Kcat, substrate specificity, substrate and/or product dissociation rates, specific label insensitivity, i.e., creating analogs that have substantially the same kinetic characteristics, regardless of the labeling group included, and the like), or altered reaction characteristics for a given application, improved polymerase protective characteristics, and others.

The advantages of such compositions are readily demonstrated with reference to their use in preferred sequence by incorporation processes. Briefly, such processes utilize a nucleic acid polymerase complexed with a template sequence and complementary polymerization primer. The complex is interrogated with labeled nucleotide analogs that, when incorporated, provide a signal event that can be detected, and is thus indicative of incorporation. Different types of nucleotides, i.e., bearing different bases, e.g., A, T, G or C, bear differentially detectable labels, such as spectrally distinguishable fluorescent dyes, permitting detection of a signal indicative of both their identity and incorporation.

For example, certain preferred applications rely upon single molecule, real-time sequencing by incorporation methods. These methods typically employ a nucleic acid synthesis complex that includes a polymerase enzyme, e.g., a DNA polymerase, a template sequence, and a primer sequence that is complementary to at least a portion of the template sequence. In typical primer extension reactions, the polymerase extends the primer sequence by incorporating additional nucleotides that are complementary to the next nucleotide in the underlying template sequence. In the real-time monitoring processes used with the invention, the reaction employs four distinctively labeled nucleotides, e.g., each labeled with a distinguishable fluorescent label. The complexes are then configured such that upon incorporation of a given base, a characteristic optical signal is produced, that both signals an incorporation event and allows identification of the type of base incorporated.

In some cases, this configuration involves the immobilization of the complex upon a solid support, such as a planar surface, e.g., of a glass slide or other substrate, and in particularly preferred aspects, within an optically confined region on a supporting substrate, such that an incorporating nucleotide is observable for a period of time that is characteristic of that incorporation. In particular, upon incorporation, a labeled nucleotide will be retained within or proximal to the active site of the enzyme. Examples of such optically confined regions include regions at or near a surface of a transparent substrate that is illuminated using total internal reflection (TIRF) spectroscopy to illuminate only species that are very close to the substrate surface. In such systems, nucleotides that are being incorporated into a complex immobilized within the illumination region at or near the surface, will be preferentially illuminated, and as a result, distinguishable over other, non-incorporated molecules. Typically, the complexes are provided in a configuration that provides for the optical resolution of individual molecular complexes, to permit single molecule (or single complex) elucidation of nucleic acid synthesis. Such single molecule configuration may include providing complexes diluted over a surface such that sufficient space is provided between the individual complexes to provide for optical resolution. Alternatively or additionally, it may comprise immobilization of individual complexes in different confined spaces, including, for example, optically confined regions as discussed below.

In other methods, the complex may be provided immobilized within an optically confined structure, such as a zero mode waveguide (ZMW). Such ZMWs provide for an illumination region that is confined in three dimensions, as opposed to only one. In particular, a nanoscale aperture is provided through a metal cladding layer that is disposed over a transparent substrate, to define the "core" of the ZMW. This nanoscale well structurally confines the illumination to the dimensions of the core. Further, where the cross sectional dimensions of the core are in the nanoscale regime of, e.g., between about 20 and about 500 nm, it will not permit passage of light of a frequency higher than a cutoff frequency from passing through the core. Instead, light illuminating one end of the core will be subject to evanescent decay through the core, resulting in a shallow illuminated region within the core, thus confining the illumination in the third dimension. By immobilizing a complex upon the transparent "floor" of the ZMW, one can selectively illuminate and observe interactions that occur at or around the complex without excessive interference from other reagents in the overall reaction mixture. The complex is then exposed to fluorescently labeled nucleotide analogs that are preferably labeled upon a phosphate group that is released upon incorporation. This process is schematically illustrated in FIG. 1.

As shown in FIG. 1, a DNA synthesis complex 102, that includes a polymerase enzyme, a template sequence and a primer sequence, is provided immobilized on the surface of a transparent substrate 104 that forms the base of the zero mode waveguide (ZMW) 106. Upon illumination through the transparent substrate 104 with light of an appropriate excitation wavelength, a small volume of the ZMW 106 is illuminated at or near the surface of the transparent substrate 104, as indicated by dashed line 108. As fluorescently labeled nucleotide analogs 110 diffuse in and out of the illumination volume, their fluorophores will be excited and emit fluorescence, but only for a very brief period, shown as a brief spike 120 in the exemplary signal plot provided below each panel. However, upon retention by the polymerase enzyme in complex 102 for incorporation, the nucleotide analog will reside within the illumination volume for much longer, and as a result, be detectable, shown as a flash in the schematic of the complex and as a prolonged or broader signal event 122 in the corresponding signal plot. Upon incorporation, the fluorescent label that is disposed upon one of the terminal phosphate groups, e.g., beta, gamma or more distal phosphate, will be cleaved from the nucleotide and will diffuse out of the illumination volume rapidly, and will no longer contribute to the detected fluorescence. By providing each type of nucleotide with a different, distinguishable fluorescent label, one can not only identify the occurrence of a detection event, but also identify the type of base incorporated within a sequence context. See, e.g., U.S. Pat. Nos. 6,056,661, 7,052,847, 7,033,764, 7,056,676, 6,917,726, 7,013,154, 7,181,122, 7,292,742, the full disclosures of which are incorporated herein by reference in their entirety for all purposes.

In still other processes, nucleotides are used that bear one or both components of an energy transferring fluorescent dye pair. For example, in some cases, the nucleotide carries a quencher fluorophore on one portion of the nucleotide, e.g., the base, while carrying an donor fluorophore on a portion of the nucleotide that is released upon incorporation, e.g., coupled to the portion of the phosphate chain that is released. Upon incorporation and cleavage of the phosphate groups from the incorporated nucleotide, the fluorophore on the released phosphate is no longer sufficiently proximal to the quencher to remain quenched, and a fluorescent signal results (See, e.g., U.S. Pat. Nos. 6,255,083, 6,762,048, 7,229,799, the full disclosures of which are incorporated herein by reference in their entirety for all purposes).

In an alternative configuration, a donor fluorophore is provided proximal to the active site of the polymerase enzyme, e.g., coupled to the protein, while the nucleotide bears an acceptor fluorophore on a portion that is cleaved away upon incorporation, e.g., the phosphate chain. The reaction is then illuminated with light of the donor's excitation wavelength. Upon incorporation, the donor and acceptor are in sufficient proximity to affect energy transfer from the donor to the acceptor, resulting in a fluorescent signal. Following incorporation, the acceptor is released from the complex and moves out of proximity to the donor (See U.S. Pat. Nos. 6,056,661, 7,052,847, 7,033,764 and 7,056,676).

One can identify the fluorescent nucleotides that are incorporated based upon their characteristic signal profile. For example, as noted above, in the case of systems employing optical confinements like zero mode waveguides, this typically includes a longer retention time in the illumination volume as compared to non-incorporated molecules, and free phosphate-label groups. Further, based upon the spectral characteristics of the fluorescent signal, one can then identify the type of base associated with such incorporation events.

Because the basis of these processes is the interaction between a polymerase and nucleotides or nucleotide analogs during primer extension, improvements in that interaction will tend to lead to improvements to the overall processes. For example improvements of reaction kinetics between labeled nucleotides and the polymerase enzyme can provide faster incorporation, and/or longer residence times, as well as better fidelity of the enzyme toward a correctly incorporated nucleotide. That interaction may be improved from one or both directions. In particular, one may direct modifications to the polymerase and/or to the nucleotide reagents to affect this improvement.

In addition to providing improved reaction characteristics, the modified nucleotide analogs of the invention can also provide other benefits in the desired applications. For example, in some cases, the presence of excited fluorophores within an active site of an enzyme such as a polymerase, potentially can lead to damaging effects believed to stem from generation of reactive oxygen species resulting from the fluorophore being excited to and relaxing from a triplet state (See, e.g., published U.S. Patent Application No. 2007/0128133, the full disclosure of which is incorporated herein by reference in its entirety for all purposes). In certain preferred aspects, the modified nucleotide analogs of the invention are configured to maintain the fluorophore distal to the active site through its interactions with other portions of the enzyme. Nucleotide structures for accomplishing this are described in greater detail below.

II. Compositions

A. Compounds

As noted above, the compositions of the invention typically include modified nucleotide analogs that provide for an enhanced interaction between the nucleotide analog and the polymerase enzyme through a polymerase interacting component of the compound. The nucleotide compositions of the invention are generally characterized by having the general structure:

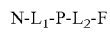

$N\text{-}L_1\text{-}P\text{-}L_2\text{-}F$ where N comprises a nucleoside polyphosphate or an analog thereof (referred to hereafter as the "nucleoside polyphosphate" portion or component); $L_1$ is a first linking group coupled to the 5' phosphate group, or its equivalent, of the nucleoside polyphosphate component; P is a polymerase interacting component; $L_2$ is a second linking group linking the polymerase interacting component to the F group, which is a labeling group.

As used herein, the nucleoside polyphosphate portion of the composition includes typical nucleoside polyphosphates and deoxynucleoside polyphosphates, including those that include naturally occurring nucleobase components, such as adenine, guanine, uracil, thymine, and cytosine. This includes typical nucleoside triphosphates adenosine, uridine, guanosine, and cytidine, as well as deoxynucleoside triphosphates, including deoxynucleoside triphosphates, which include deoxyadenosine, deoxyguaniosine, deoxythymidine, deoxycytidine and uracil. Also included are such nucleotides that include longer 5' phosphate chains, such as tetraphosphate, pentaphosphate, hexaphosphate, heptaphosphate, and longer phosphate chain analogs. Also included within this portion of the compositions are other nucleotide analogs, such as peptide nucleic acid monomers (PNAs), locked nucleic acid monomers (LNAs), and the like.

The first linking group $L_1$ is generally any linking group or groups that couple the 5' portion of the nucleoside polyphosphate portion to the polymerase interacting component "P". Such linkages may include individual atoms such as O, N, S, or the like, or may even be a chemical bond, e.g., a single, double or triple bond. Alternatively, and preferably, longer linkages may be employed, such as alkyl, aminoalkyl, alkoxyl, aryl, polyaryl, or multimeric linker groups, such as nucleic acid linkers, peptidyl linkers, polyethylene glycol linkers, or other appropriate linkages.

The polymerase interacting component of the compositions of the invention includes molecular groups that interact with corresponding proximal groups on the polymerase enzyme during primer extension. Nucleic acid polymerases, as evidenced by their activity for common substrates, nucleotides (including deoxy- and dideoxynucleotides), also share a number of structural characteristics, particularly within or around their active sites. For example, a number of polymerases derived from bacteriophages share a number of conserved structural traits, particularly in residues that are proximal to the active site in the three dimensional structure of the protein. By way of example, the catalytic center of a DNA polymerase 200, shown as a three dimensional model structure in FIG. 9, includes two hydrophobic residues at and around the 375 and 512 positions, 202. Both of these regions fall within interactive distance of a nucleotide analog 204 retained within the active site pocket of the polymerase, and particularly a hydrophobic labeling group on that analog. Typically, interactive distances, for purposes of, e.g., Van der Waals interactions, will fall in the range of from about 3 to about 5 angstroms between the polymerase interacting component and those portions of the polymerase with which the interacting component interacts. By configuring an analog with a polymerase interacting component that interacts with one or more of the specific charge distribution or hydrophilic or hydrophobic nature of these regions, one would expect to enhance the interactivity between the analogs and the polymerase.

In a particular exemplary system including certain modified or engineered polymerases, residues that correspond with the general positions described above, have been modified to include hydrophobic tyrosine residues (See published U.S. Patent Application No. 2007/0196846, incorporated herein by reference in its entirety for all purposes). In this case, complementary or interacting hydrophobic groups are employed in the nucleotide at the polymerase interacting component.

Based upon the foregoing, it will be appreciated that the polymerase interacting component (P or P') may vary depending upon the three dimensional structure of the polymerase enzyme being employed. In general, however, such interacting components will comprise one or more of positively charged groups, negatively charged groups, hydrophobic groups, hydrophilic groups, and/or hydrogen bonding groups, depending upon the specific stricture of the polymerase being employed.

By way of example, where a polymerase includes positively charged groups most proximal to the polymerase interacting component when the analog is within the active site of the enzyme, the polymerase interacting component may comprise a negatively charged group to provide an enhanced interaction between the polymerase and the nucleotide analog. Some exemplary charged groups that could be incorporated into the nucleotide compositions of the invention include, e.g., positively charged groups such as guanidinium, ammonium, iminium, oxonium or the like, and/or negatively charged groups, such as carboxyl, phosphate, phosphonate, thio, sulfate, sulfonate, thioate, phosphothioate groups, and the like.

Likewise, where the polymerase includes hydrophobic moieties that are most proximal to this portion of a nucleotide analog during binding, then the interactive group of the nucleotide analog will typically include hydrophobic groups to favorably interact with their counterparts on the polymerase. A variety of different hydrophobic groups can be incorporated into the general structure of the nucleotide analog shown above, including, e.g., alkyl, aryl (including polyaryl groups), heteroaryl, cycloalkyl, bicycloalkyl, and other groups. Examples of preferred hydrophobic groups include phenyl groups, biphenyl groups or triphenyl groups, heteroaryl groups and the like. A general structure of a preferred biphenyl polymerase interacting component is illustrated by the following structure:

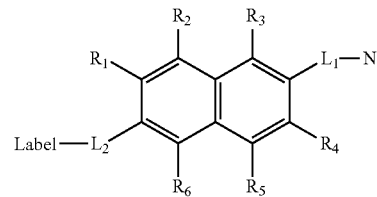

where $R_1$ through $R_6$ are independently selected from H, O, OH, positively charge groups such as guanidinium, ammonium iminium, oxonium or the like, and/or negatively charged groups such as carboxyl, phosphate, phosphonate, thio, sulfate, sulfonate, thioate, phosphothioate groups, and the like. Similarly, a general structure of an exemplary heteroaryl structure includes a coumarin derivative polymerase interacting component, such as a chromene, 2-chromanone, 2H-chromene, or 2H-chromen-2-none. One exemplary polymerase interacting component has the general structure:

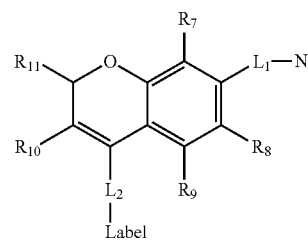

As with the biphenyl group illustrated previously, the side chain substituents of the polymerase interacting component shown above (i.e., $R_7$ through $R_{11}$), are generally independently selected from the groups set forth for groups $R_1$ through $R_6$, above. For certain polymerase enzymes, e.g., those having two tyrosine residues proximal to the active site (as set forth above), enhanced interactivity is produced by providing a negatively charged group, such as $SO_3$, $PO_3$, OH, or the like, or a hydrogen bonding group, e.g., double bonded O, at the $R_{11}$ position to yield improved interactivity and thus improved reaction characteristics.

As above, where the polymerase molecule possesses hydrophilic moieties at these points, then similarly hydrophilic groups may be employed in the polymerase interacting component on the nucleotide analog, e.g., amine, carboxyl, guanidinium, thioates, etc.

While generally described as being either hydrophobic, charged, or the like, it will be appreciated that the polymerase interacting component may comprise more than one basis of interactivity with the polymerase, including, for example, charged hydrophobic groups, groups with variable local charge distributions, e.g., both positive and negative, and the like.

In the structures illustrated above, the polymerase interacting component is linked to the labeling group F through linking group $L_2$. Again, linking group $L_1$ may be selected from any of a variety of different types of linking groups, as with $L_1$, above. In preferred aspects, adjustable length linking groups are used to provide linkage of the labeling group to the rest of the compound, such as alkyl, aryl, peptidyl, or oligonucleotide based linkages. For example, in certain preferred aspects, methyl, ethyl, butyl, propyl, pentyl, hexyl, or longer chain alkyl groups are employed as the second linking group, thus allowing facile modification of the distance of the labeling group from the polymerase interacting component. The linker groups may be coupled through any conventional linkage technique, including, for example, an amide linkage generated through standard NHS chemistry (see below).

Although generally illustrated in a serial linkage, e.g., -$L_1$-P-$L_2$-F, it will be appreciated that the polymerase interacting component may include a linkage component between $L_1$ and $L_2$ that does not, itself provide for interaction with the polymerase. As such, the foregoing structure encompasses the structure where the interacting portion of the polymerase interaction component may be provided as a side chain component, such as in the partial structure illustrated below:

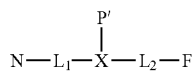

where X is a linkage component of the polymerase interacting component and P' is the portion of the polymerase interacting component that functionally interacts with the polymerase enzyme, e.g., X and P' together make up the "P" group from the linear structure set forth above.

Based upon the foregoing, therefore, one may schematically illustrate the structure of certain compounds of the invention as:

where Y comprises a polymerase interacting linkage complex that joins the nucleotide component to the labeling component, and may be for example, the $L_1$-P-$L_2$ or $L_1$-X(P')-$L_2$ structure illustrated above.

Figure 3:
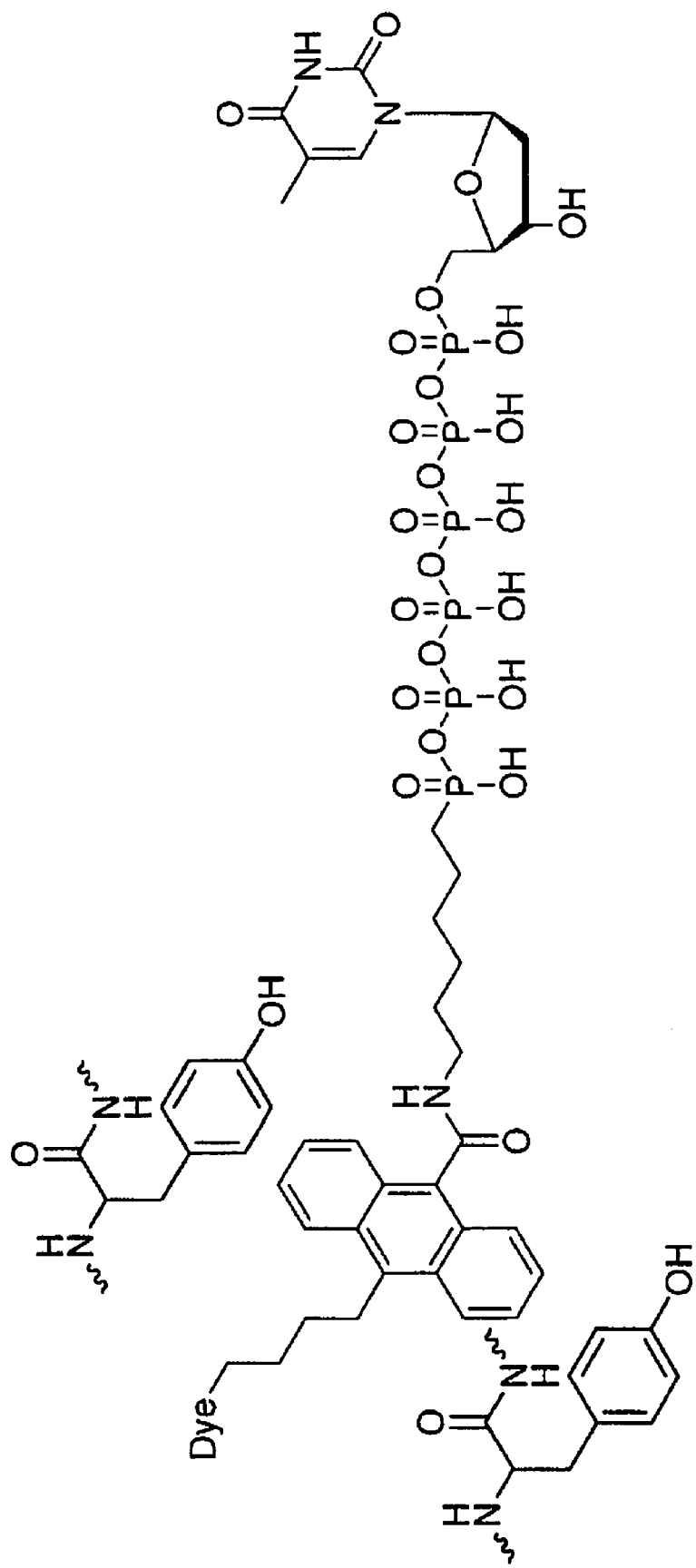
FIG. 3 provides a schematic illustration of an exemplary compound of the invention and its expected interaction with certain polymerase residues.

FIG. 3 provides a schematic illustration of a compound of the invention that includes a triphenyl group within the polymerase interacting component in conjunction with the predicted location of the two tyrosine residues of the modified polymerase enzyme.

As will be appreciated from the present disclosure, polymerase interacting components will typically be positioned to be appropriately proximal to the portions of the polymerase with which interaction is sought, e.g., charged or hydrophobic residues around the active site of the polymerase. Restated, the linkage between the nucleoside polyphosphate component of the compound and the polymerase interacting component will typically be selected to appropriately position the interacting component sufficiently proximal to the particular residues in the polymerase to provide functional interaction, e.g., higher affinity, leading to better reaction kinetics. For example, in the case of the polymerase structure illustrated in FIG. 2, it is expected that the requisite distance from the nucleoside component to the polymerase interacting component will typically be from about 20 to about 40 angstroms. Factoring in the length of each phosphate group (approximately 2.72 angstroms), the polyphosphate chain may account for from about 8.16 angstroms to about 19.04 angstroms of this distance, depending upon whether a nucleoside tri-, tetra-, penta-, hexa- or even heptaphosphate is used as the nucleoside polyphosphate component. In preferred aspects, a tri, tetra, penta or hexaphosphate is used, so that the phosphate distance is approximately 8.16, 10.88, 13.60 or 16.32 angstroms, respectively. Accordingly, linking group $L_1$ will typically the selected to make up for the remaining desired distance, e.g., from about 4 to about 32 angstroms.

Figure 2:
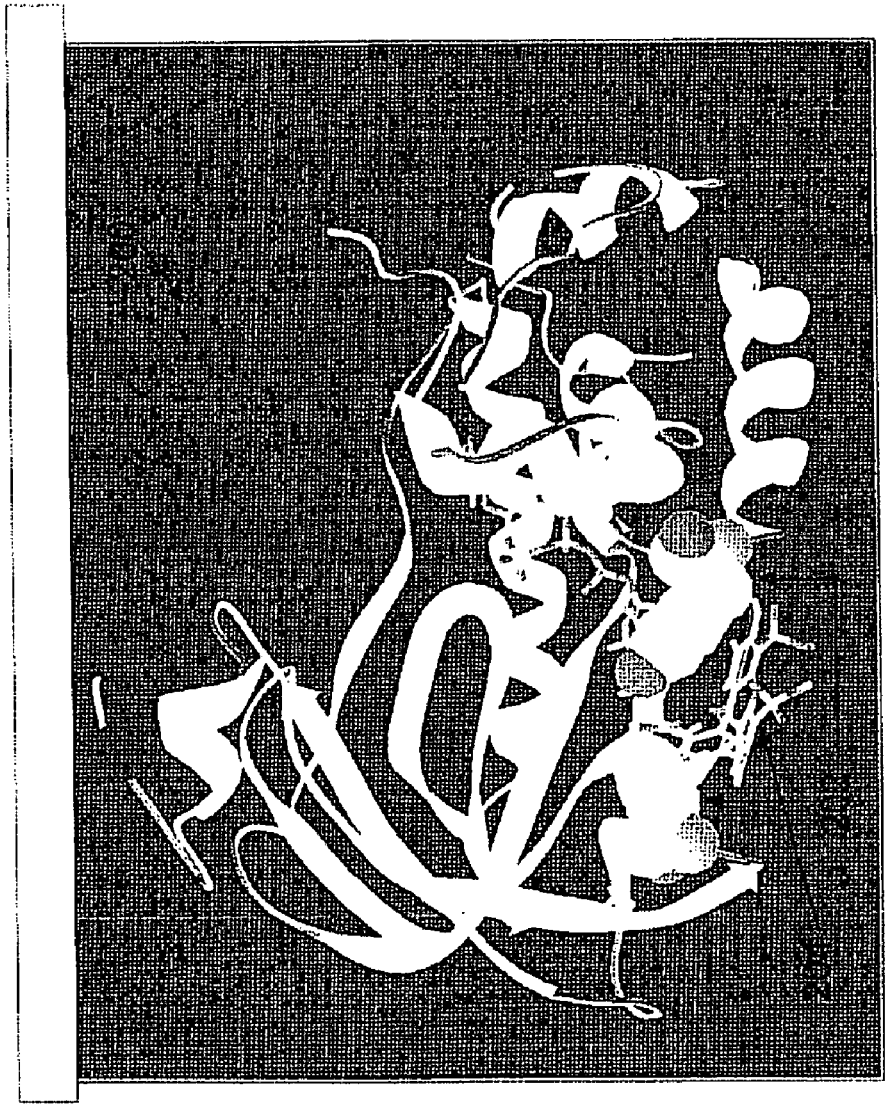
FIG. 2 provides a three dimensional model image of a nucleic acid polymerase active derived from a Phi29 bacteriophage.

For many polymerase enzymes for which the three dimensional structure has been elucidated, the distance between the active site and potentially interacting residues is expected to be approximately equivalent to the modeled structure shown in FIG. 2, such that a distance between a nucleoside component and a polymerase interacting component of between about 20 angstroms and about 40 angstroms, and preferably, 20 to 30 angstroms, will be applicable. For example, for certain polymerases described elsewhere herein, e.g., phi29 or other polymerases, the distance between the nitrogen of a nucleobase in a retained nucleotide and the residues identified elsewhere herein is approximately 27 angstroms, based upon three dimensional models of the enzyme.

As noted above, the present invention provides compositions that include nucleotide analogs that desirably interact with the polymerase enzymes with which they are reacting through the inclusion of a polymerase interacting component in the nucleotide analog compound. As noted above, the nature of the interacting component will depend upon the portions of the polymerase enzyme with which it interacts. For example, the active sites of polymerase enzymes will often include a number of conserved features, such as a binding groove, trough or funnel in which sits the template primer complex during synthesis. In a specific example, a number of bacteriophage derived polymerases share some common structural characteristics at positions proximal to the active site. For example, FIG. 4 shows a sequence alignment among five different bacteriophage polymerases (B103, M2, GA1, Phi29, and B. subtilis phage PZA. See Meijer et al., Microbiol Mol Biol Rev. 2001 June; 65(2): 261-287). Just looking at those residues that correspond in position to those noted above (375 and 512), one can readily observe common charge characteristics among the various polymerases. In particular, these residues are charged and hydrophilic, and are predominantly negatively charged at the 375 residue and positively charged at the 512 residue. Accordingly, it would be expected that common polymerase interacting components may be readily employed for each of these types of polymerases. In particular, one may provide a bifunctional interacting component, e.g., being partially charged at one end and oppositely charged at the other end, or alternatively, bearing hydrophobic moieties at one end while providing hydrophilic moieties or charge moieties at the other end. Further, identification off other common interacting features around the active site can provide additional avenues for interactivity.

While the general structure of the compounds of the invention is described above, specific exemplary structures are provided below. In particular, the structures of the nucleoside polyphosphate portion of the compound will typically comprise a nucleobase portion coupled to a sugar moiety, such as a ribosyl group at the 1' position, and a 5' phosphate chain that may include 3, 4, 5, or more phosphate groups. An exemplary nucleoside polyphosphate structure includes:

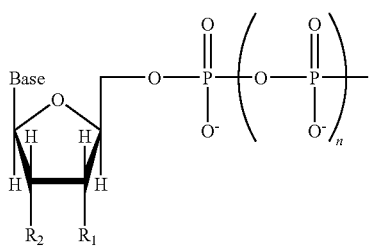

where $R_1$ and $R_2$ are independently selected from H and OH, and $R_1$ is preferably OH; Base is a nucleobase selected from adenine, guanine, thymine, cytosine, uracil, inosine and the like; n is 2 or greater, and preferably is selected from 9, 3, 4, 5 or 6. Although illustrated as $O^-$, the substituents on each of the phosphate groups present are also optionally independently selected from other groups such as $BH_3$ and S.

The linking groups $L_1$ and $L_2$, that link the nucleoside polyphosphate portion of the molecule to the polymerase interacting component, or the polymerase interacting component to the labeling group may independently comprise single bonds, single atoms or larger molecules. For example $L_1$ and $L_2$ may be independently selected from O, N, S, or the like, or they may include larger structures, such as alkyl, aminoalkyl, alkoxyl, aryl, polyaryl, or multimeric linker groups, such as or other larger linkages. Multimeric linkages are also envisioned as linking groups for one or both of $L_1$ and $L_2$, including, e.g., vinyl groups, nucleic acid linkers, peptidyl linkers, polyethylene glycol linkers, polybenzyl or other polyaryl groups, or other appropriate linkages. In preferred aspects, the linking groups $L_1$ and $L_2$ will be independently selected from individual atoms, such as O, N or S, alkyl groups of from 1 to 18 carbons in length, including substituted alkyl groups, such as aminoalkyl linkers. Optionally, alkoxy groups of from 1 10 18 carbons are employed as linkers. In certain exemplary embodiments, aminohexyl groups are employed as linkers alone or in conjunction with longer alkoxy groups, such as aminohexyl-aminoheptanoic acid linkers or the like. As will be apparent from the instant disclosure, one can employ a variety of linker chemistries in coupling the various groups of the compound of the invention together.

The labeling group F is typically a readily detectable labeling group, such as a luminescent, fluorescent, fluorogenic, chromogenic, magnetic, radioactive or other type of detectable label. In preferred aspects, the labeling group F is selected from fluorescent labeling groups including individual fluorophores and cooperative fluorophores, e.g., one or both members of a donor-quencher or FRET pair. In the case where F is at least one member of a cooperative fluorophore pair, the second member of the pair may also be included within the F group, e.g., as a unified FRET dye structure (See, e.g., U.S. Pat. No. 5,688,648 for a discussion of FRET dyes), or it may be provided elsewhere on the analog or the overall system. For example, in some cases, the other member of the pair may be coupled to and as a portion of the Base moiety attached to the sugar group (See, e.g., U.S. Pat. No. 6,232,075 previously incorporated herein by reference). Alternatively, the other member of the pair may be coupled to another reaction component, e.g., a polymerase enzyme (See, e.g., U.S. Pat. No. 7,056,676, previously incorporated herein by reference).

A wide variety of different types of fluorophores are readily available and applicable to the compounds of the invention and include fluorescein, or rhodamine based dyes, cyanine dyes and the like. A variety of such dyes are commercially available and include the Cy dyes available from GE Healthcare (Piscataway, N.J.), such as Cy3, Cy5, and the like, or the Alexa® family of dyes available from Invitrogen/Molecular Probes (Carlsbad, Calif.), such as Alexa 488, 500, 514, 532, 546, 555, 568, 594, 610, 633, 647, 660, 680, 700, and 750. These fluorophores may be present as individual fluorophores or they may be present in interactive pairs or groups, e.g., as fluorescent resonant energy transfer (FRET) pairs.

Alternative labeling strategies may employ inorganic materials as labeling moieties, such as fluorescent or luminescent nanoparticles, e.g. nanocrystals, i.e. Quantum Dots, that possess inherent fluorescent capabilities due to their semiconductor make up and size in the nanoscale regime (See, e.g., U.S. Pat. Nos. 6,861,155, 6,699,723, 7,235,361). Such nanocrystal materials are generally commercially available from, e.g., Invitrogen, Inc., (Calsbad Calif.). Again, such compounds may be present as individual labeling groups or as interactive groups or pairs, e.g., with other inorganic nanocrystals or organic fluorophores.

Again, the labeling group may be directly coupled to the polymerase interacting component, e.g., the hydrophobic group, or it may be coupled through a longer linking group. Such linking groups include those described above, such as alkyl, aryl, peptidyl, and the like, as well as the aforementioned multimeric linking groups.

Figure 5:
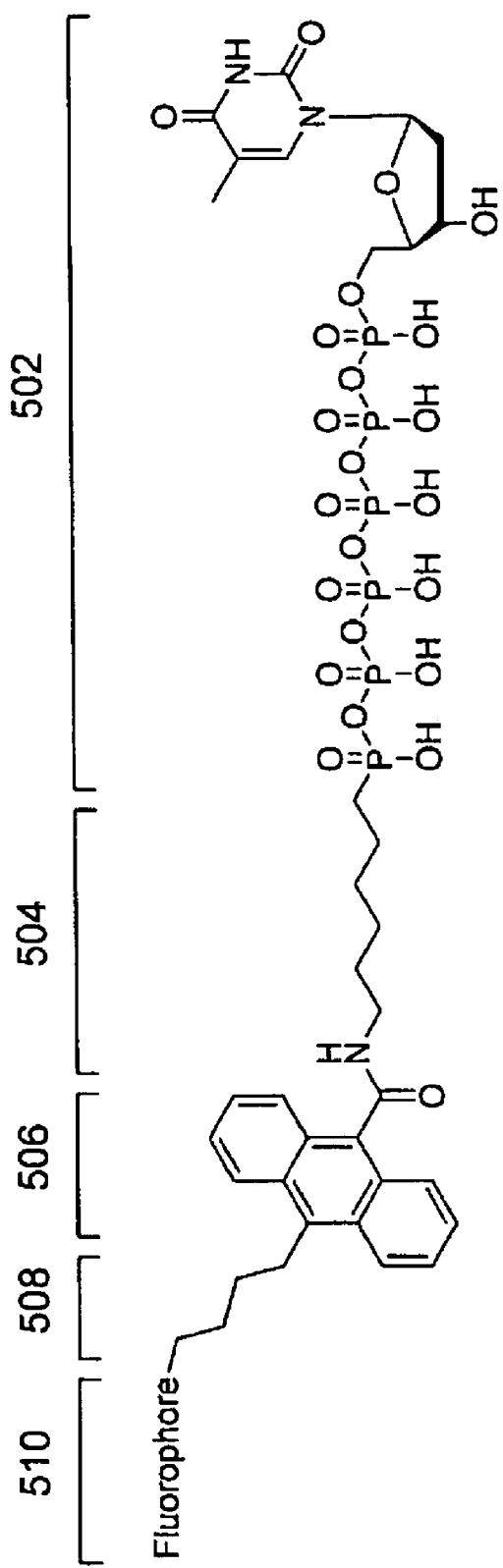
FIG. 5 provides a schematic illustration of a compound of the invention highlighting the structural components thereof.

FIG. 5 schematically illustrates one exemplary compound of the invention along with a legend indicating the different constituent components. In particular, the compound shown provides a nucleoside polyphosphate component 502 that is comprised of a deoxythymidine pentaphosphate. The nucleoside polyphosphate component 502 is linked, via an aminohexyl linking group 504 to the polymerase interacting component 506, shown as a triphenyl group. This triphenyl group is, in turn, coupled to a fluorophore 510 via another alkyl linker group 508.

Figure 6:
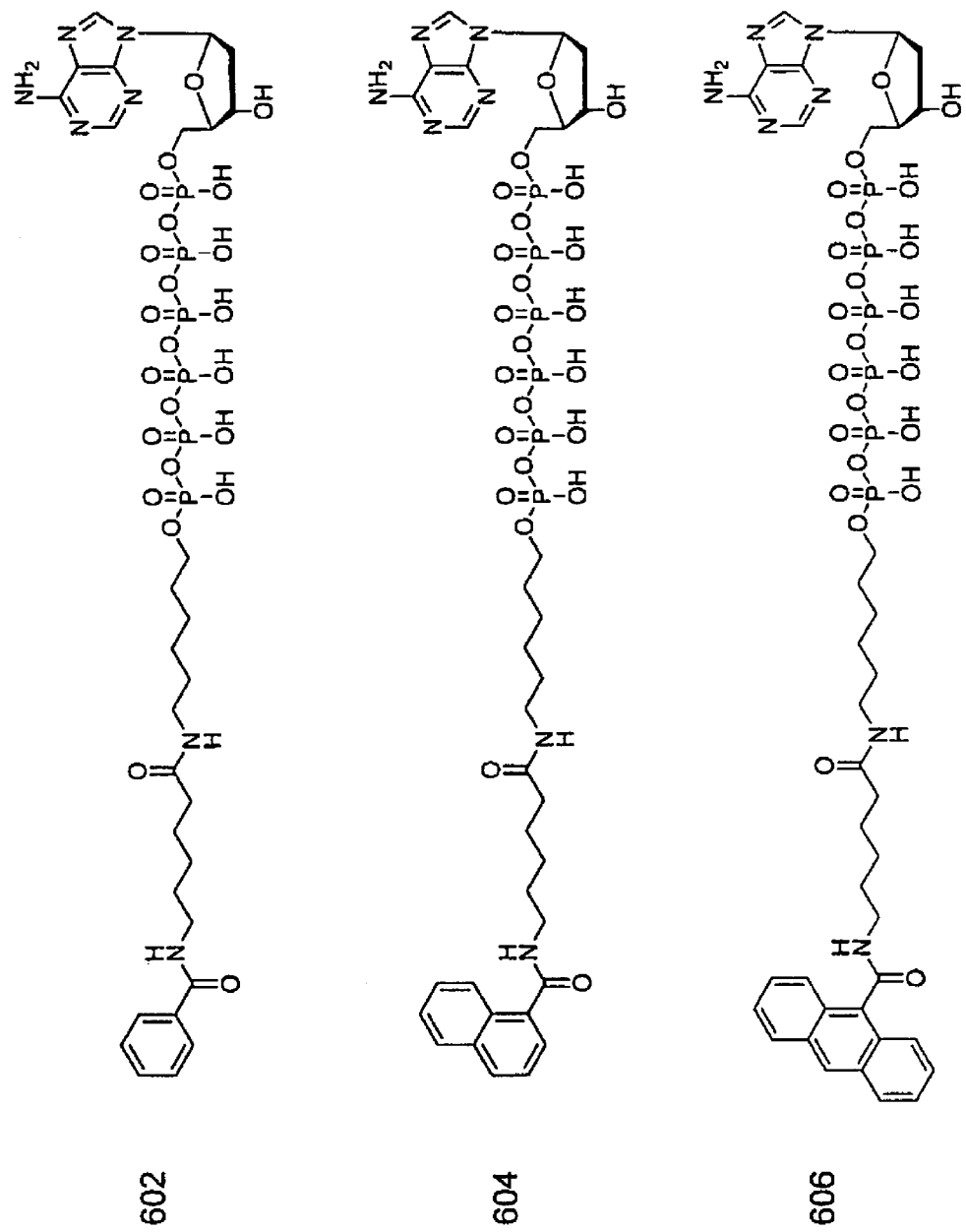
FIG. 6 schematically illustrates three compounds of the invention incorporating three different hydrophobic polymerase interacting components.

FIG. 6 illustrates a side by side comparison of nucleoside hexaphosphates having aminohexyl aminoheptanoic acid linkers coupling the nucleoside to different hydrophobic polymerase interacting components. In particular shown are compounds that includes a benzyl group (compound 602), a naplithyl group (compound 604), and an antiracyl group (compound 606).

Figure 7:
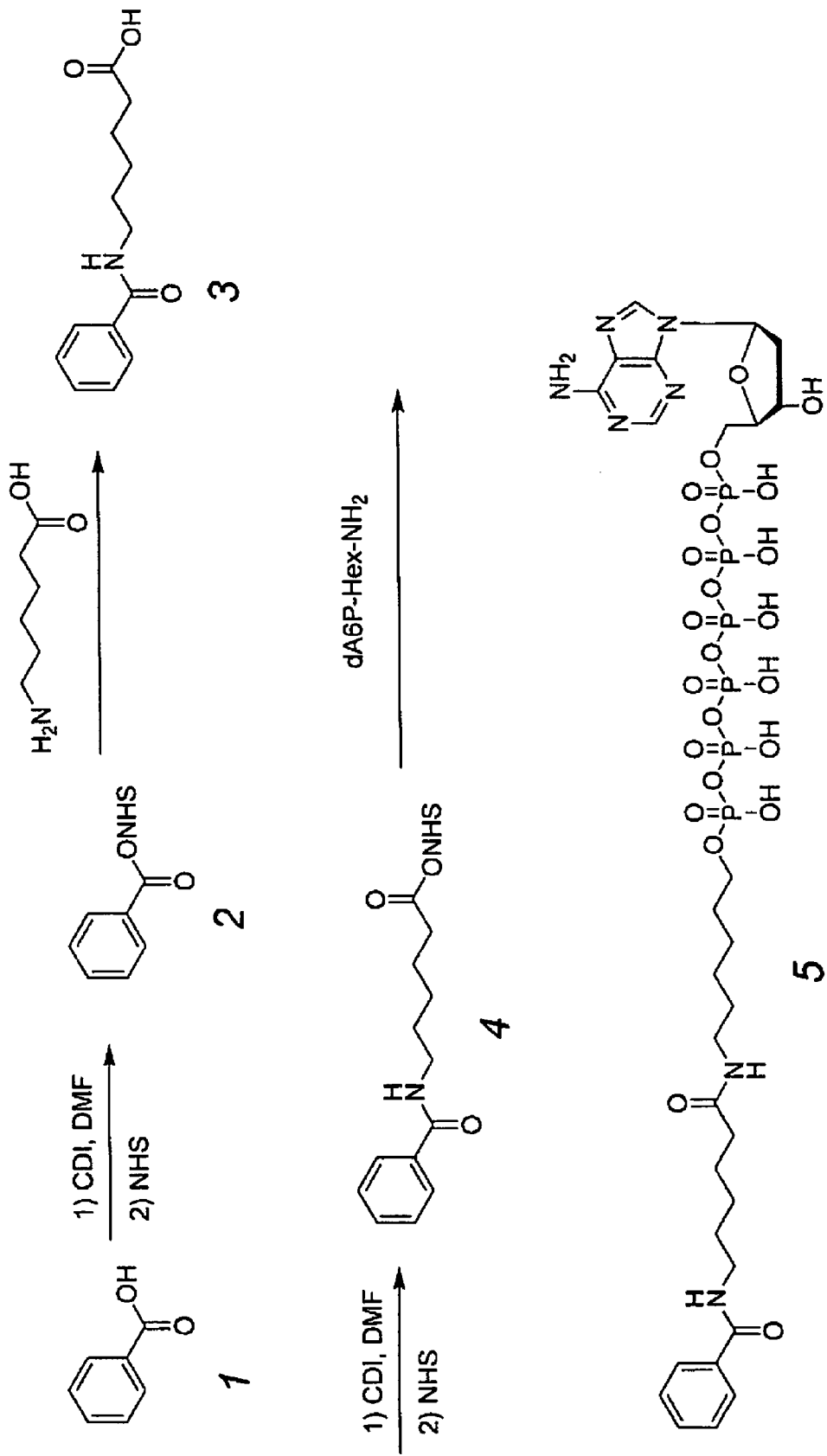
FIG. 7 illustrates a synthetic scheme for a compound of the invention.

FIG. 7 schematically illustrates the synthesis scheme for the compound illustrated as compound 602 in FIG. 6. In particular, as shown, a reaction of benzoic acid (1) with 1,1'-carbonyldiimidazole (CDI) and N-hydroxysuccinimide (NHS) in DMF gave the activated benzoyl NHS ester (2) which is then reacted with aminocaproic acid to give the coupling product (3). Again, activation using the CDI/NHS chemistry gave the activated NHS ester (4) which is then reacted with aminohexyl deoxynadenosine hexaphosphate to give the target product, benzene-XX-dA6P (5).

Figure 8:
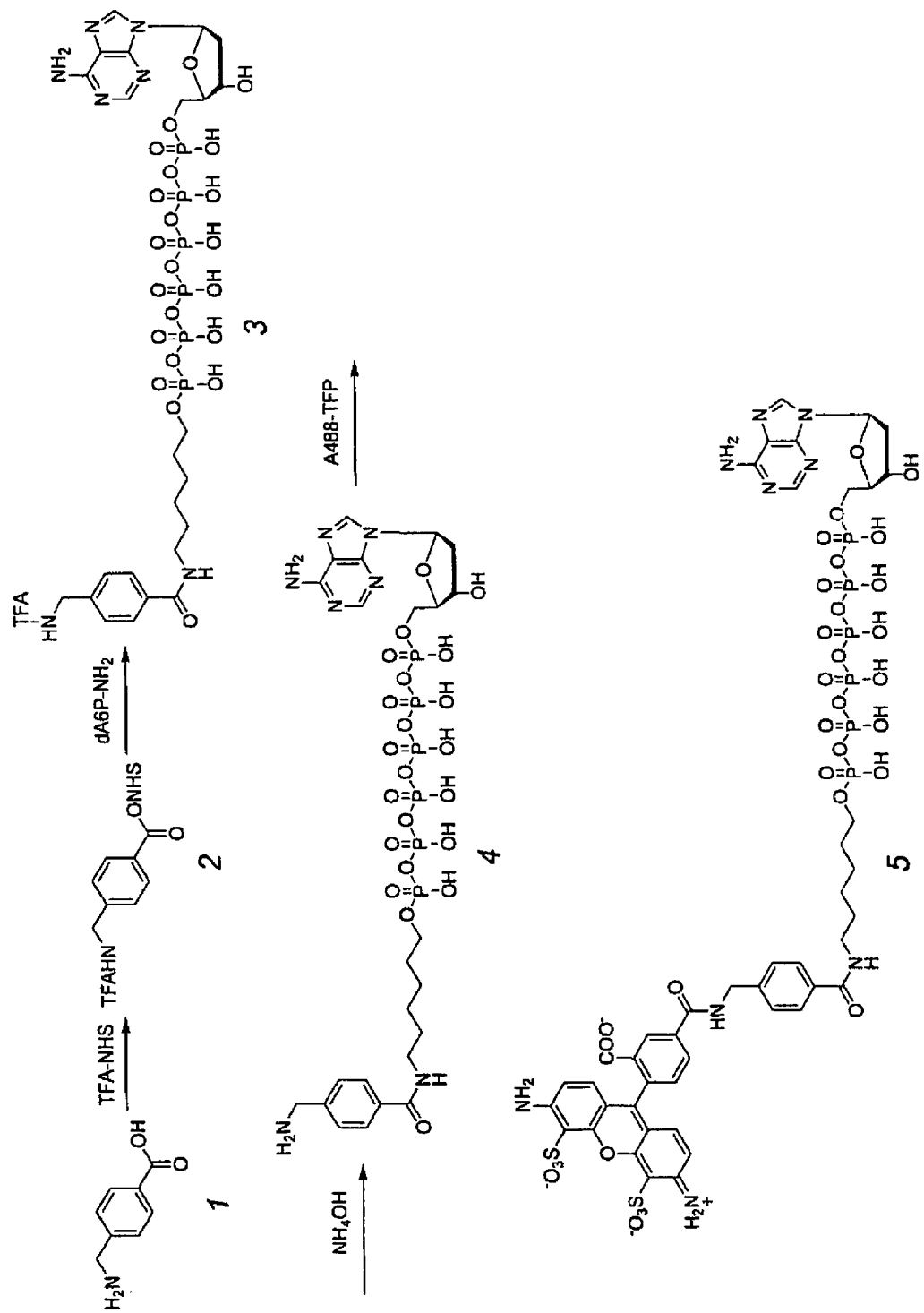
FIG. 8 provides an exemplary synthetic scheme for coupling fluorescent dye moieties to the compounds of the invention.

FIG. 8 provides an exemplary synthetic scheme for coupling fluorescent dyes to an exemplary compound (compound 602). Again, as shown, a reaction of aminomethylbenzoic acid (1) with TFA-NHS provides the TFA protected NHS activated ester (2) which is then reacted with aminohexyl deoxynadenosine hexaphosphate to give the adduct (3). Deprotection of the adduct (3) with ammonium hydroxide gives the amino nucleotide (4). Reaction of (4) with Alexa48X-TFP in 0.1 M $NaHCO_3$ buffer solution gives the dye labeled nucleotide (5) after HPLC purification.

Figure 9:
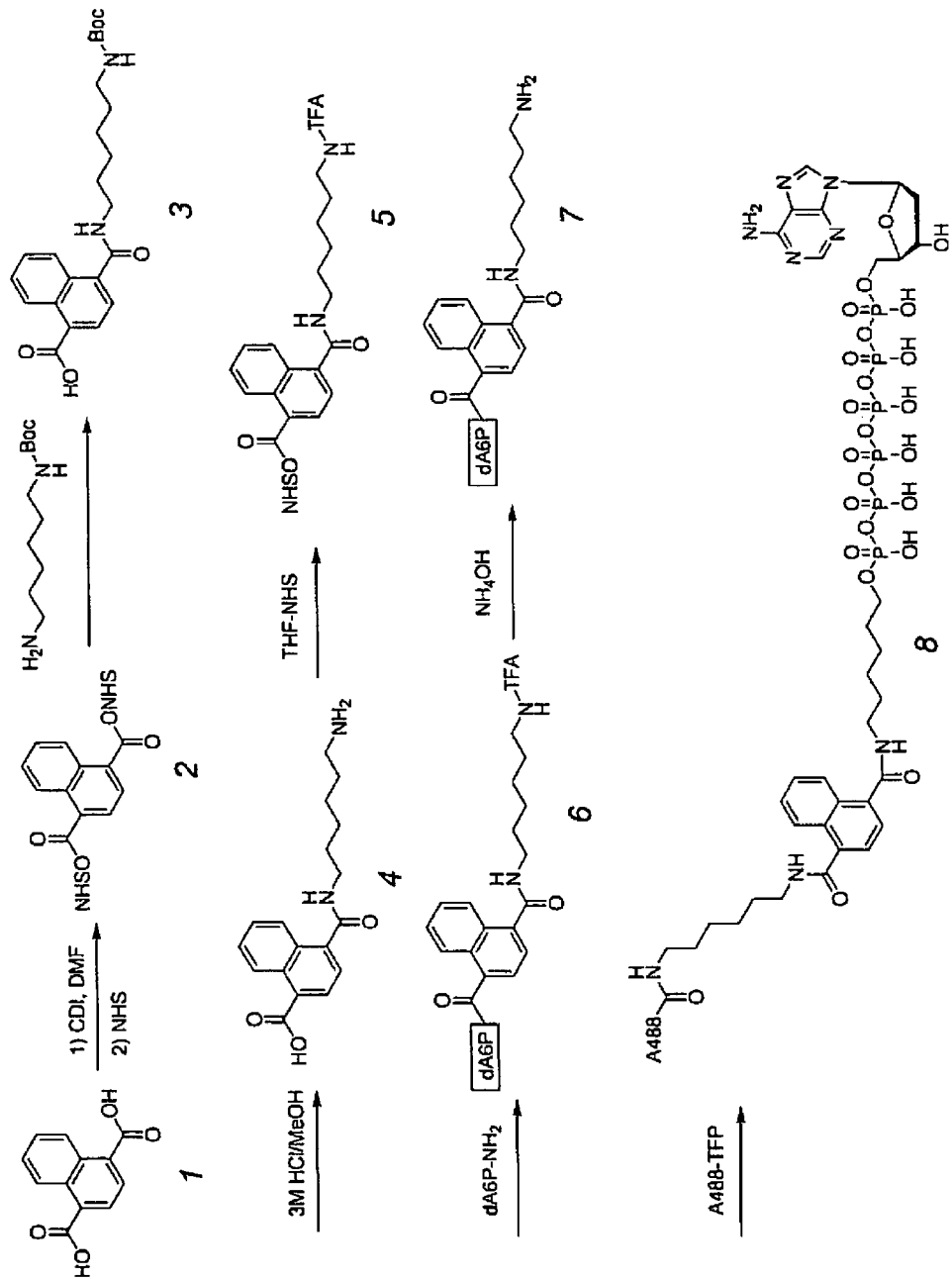
FIG. 9 illustrates an alternative synthetic scheme for synthesizing compounds of the invention.

An alternative synthetic scheme is illustrated in FIG. 9 for generation of a dye labeled nucleotide analog having a biphenyl or napthyl polymerase interacting component. As shown, activation of naphthalene-1,4-dicarboxylic acid (1) with CDI/NHS gives the bis-NHS ester (2), which is then reacted with one equivalent of mono Boc protected 1,6-hexanediamine to give the mono adduct (3). Deprotection of Boc group with 3M HCl in a 1:1 water:MeOH solution gives the aminoacid (4). Protection of the amino group and activation of the carboxylic acid group can be done with the TFA-NHS reagent to give the activated ester (5), which is then reacted with aminohexyl deoxyadenosine hexaphosphate following by the ammonium hydroxide deprotection to give the adduct (7). Reaction of the amino compound (7) with Alexa488-TFP in 0.1 M NaHCO₃ buffer solution gives the dye labeled nucleotide, compound (8), after HPLC purification.

An exemplary compound of the invention is provided by the structure:

groups, such as semiconductor nanocrystals, or other fluorescent or fluorogenic particles. As will be appreciated, the base will typically comprise any nucleobase, and preferably nucleobases associated with ribonucleotides and deoxyribonucleotides. Also, while illustrated as a triphosphate compound, it will be appreciated that polyphosphates with more than three phosphate groups are also envisioned in the context of the invention, e.g., where n is 1 or greater, e.g., 1, 2, 3, 4, 5 or greater. Likewise, although illustrated as PO₃ groups within the polyphosphate chain, it will be appreciated that the

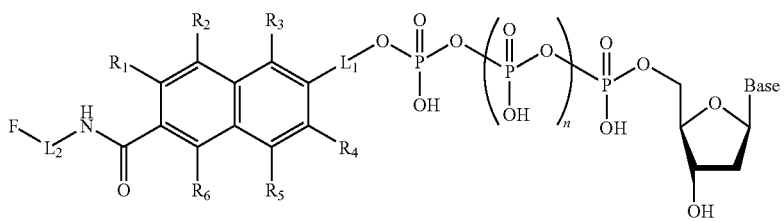

where $R_1$ through $R_6$ are as described above. As will be appreciated, these groups may generally be modified to adjust the electrostatic interaction by substituting one or more of these groups with electron rich or poor groups to interact with specific residues for the polymerase enzyme being used. $L_1$ may comprise a direct bond between the terminal oxygen and the aromatic interacting component, or it may comprise multiple atoms, such as in a simple alkyl linkage of variable length, PEO linkers, PEG linkers or any of a variety of other linker groups. Likewise the linker between the labeling component F and the aromatic interacting component may be comprised of any of a variety of different linker types. As above, the label group (F) comprises a detectable labeling group, such as a fluorescent or luminescent labeling group, or alternatively, an electrochemically detectable group, such as a charged or magnetic moiety, particle or the like. Fluorescent labeling groups are generally preferred for the ease of detection, high quantum yield, and ease of linking with nucleotide compounds. Such fluorescent compounds include small molecule fluorophores, as well as particle based fluorescent oxygen side chains may be substituted with any of a number of other groups, and still fall within the scope of the invention. For example, oxygen side groups may generally be substituted with a variety of other groups, such as sulfur, boron, or others, while still allowing their use as substrates for polymerase enzymes.

In alternate cases, one may substitute the biphenyl polymerase interacting component with a coumarin group to yield, e.g., the compound:

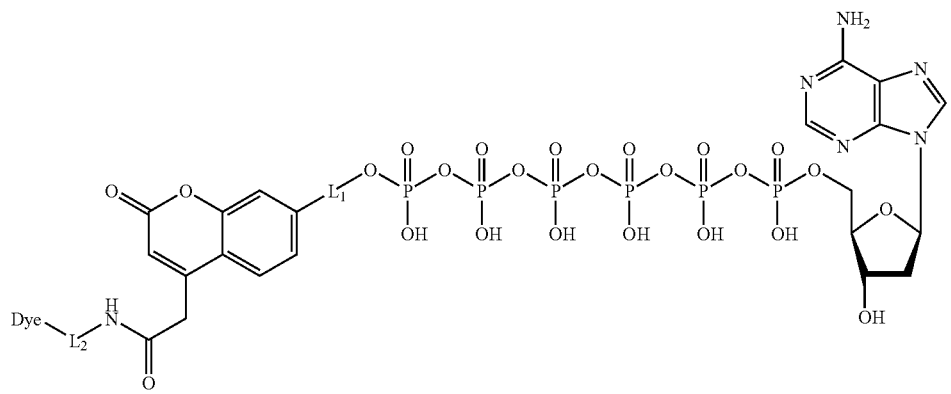

Figure 10:
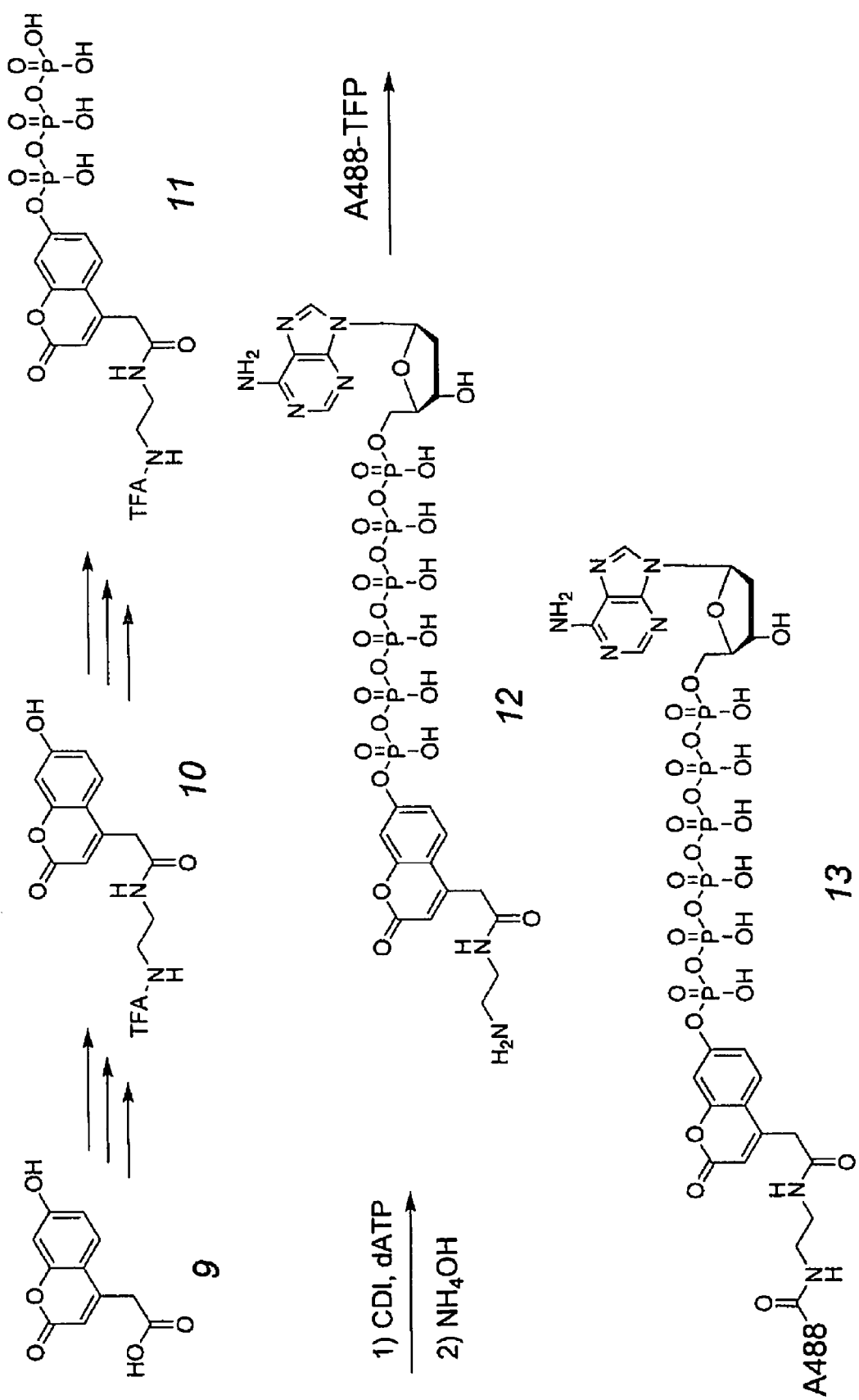
FIG. 10 illustrates a synthetic scheme for compounds of the invention.

FIG. 10 provides an exemplary synthetic scheme for the compound illustrated above. Activation of 7-hydroxycoumarin-4-acetic acid (9) with CDI/NHS followed by reaction with ethylenediamine and subsequent protection of the amino group gives the hydroxycoumarin (10). Reaction of (10) with POCl3 and then pyrophosphate gives the corresponding triphosphate (11). Again, activation of (11) with CDI and reaction with dATP followed by ammonium hydroxide deprotection gives the amino-cumarin-dA6P (12). Reaction of amino-cumarin-dA6P (12) with fluorescent dye A488-TFP gives the dye labeled nucleotide, compound (13), after HPLC purification.

Figure 13:
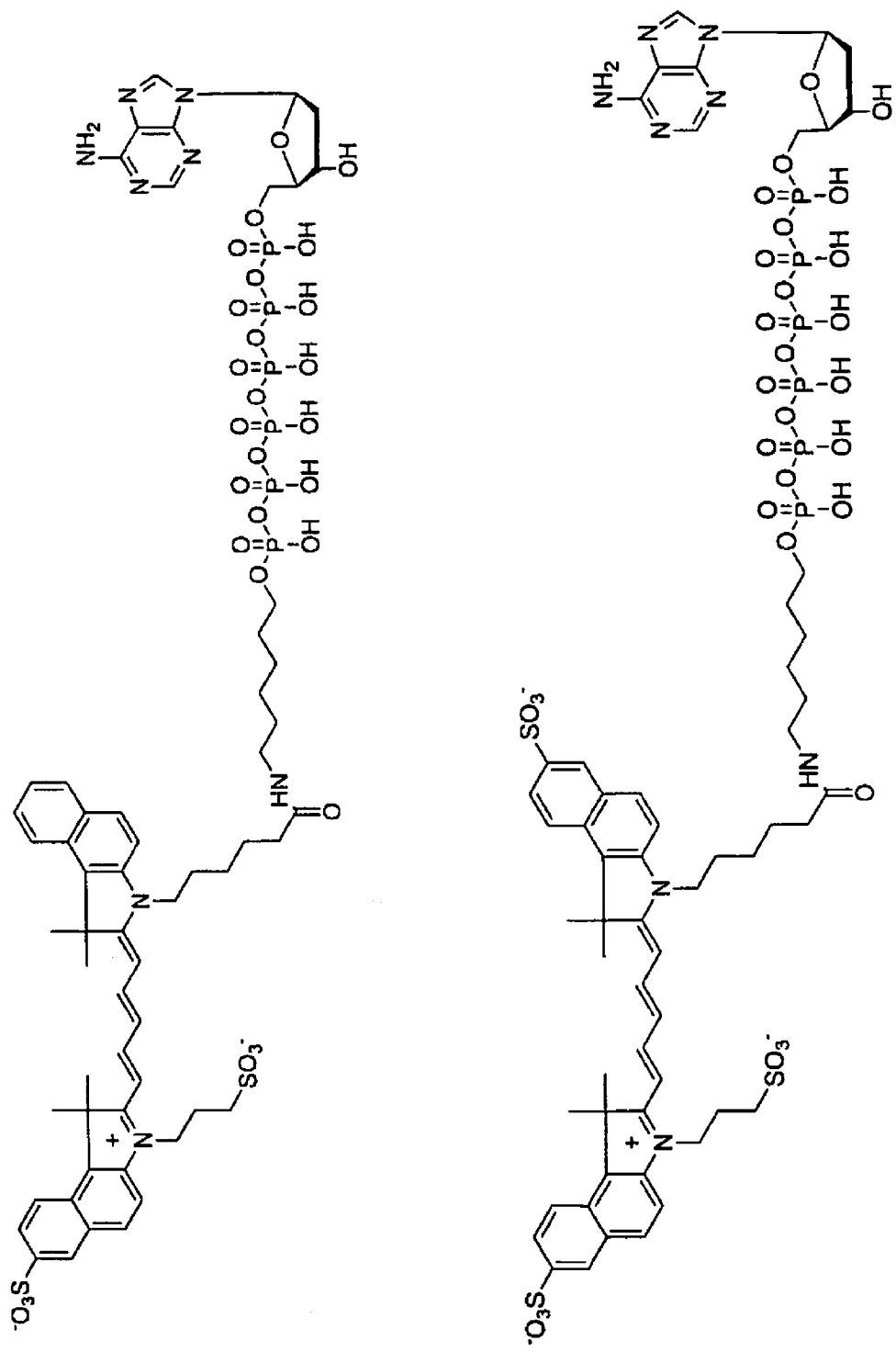
FIG. 13 schematically illustrates an alternative compound configuration in which a polymerase interacting component is engineered into the labeling moiety.

While described in terms of the label component and the polymerase interacting component as being separate and discrete groups within the overall structure of the compounds of the invention, it will be appreciated that certain aspects of the invention may include polymerase interacting components in the label portion itself. In particular, as many fluorescent compounds are larger molecules, they provide significant opportunity to adjust local properties of the overall compound. By way of example, a labeled compound may be provided that includes polymerase interacting functionality integrated into the dye or label molecule. Such interacting capability includes those described above, e.g., hydrophobicity, charge (positive and/or negative), and bifunctional characteristics. Examples of bifunctional characteristics integrated into a labeling component are shown in, e.g., FIG. 13. In particular, shown are two fluorescently labeled nucleotide analogs, in which charged moieties (sulfonate groups) are coupled to portions of the label that would be expected to interact with oppositely charged polymerase components. As shown, the top compound (Panel I) includes a doubly charged labeling compound, while the second compound (panel II) includes 3 charged groups.

B. Compound/Polymerases

The compounds of the invention are typically applied in conjunction with other reaction components, but particularly with their complementary polymerase enzymes. As used herein, a complementary polymerase enzyme for a given embodiment of the compounds of the invention is a polymerase that includes a portion that interacts with the polymerase interacting component of the compound, when that compound is retained within the active site of that polymerase.

By way of example, for the compound illustrated in FIG. 3, one complementary polymerase enzyme would be that shown in FIG. 2, having two tyrosine moieties disposed at the 375 and 512 positions, and proximal to the triphenyl group of that nucleotide analog when it is retained within the active site (as shown in FIG. 3), giving rise to a desirable hydrophobic interaction between the analog and the polymerase. Moreover, other complementary polymerases for the nucleotide analog shown in FIG. 3, or those nucleotide analogs having other hydrophobic polymerase interacting groups, will also typically possess hydrophobic residues at similar locations in the three dimensional structure of the polymerases' active site.

In contrast, complementary polymerases to nucleotide analogs that have positively or negatively charged groups in the position of the polymerase interacting component may generally have oppositely charged groups proximal to such position on the nucleotide analog, when that analog is retained within the active site of the polymerase.

As will be appreciated, the compositions of the invention may generally be broadly useful in a range of different polymerase systems. For example, as noted above, reactions employing phage derived polymerases, such as Φ29 DNA polymerase or mutant thereof, may be benefited from the use of the compositions described herein. Other polymerases include, for example, Taq polymerases or derivatives thereof, DNA Pol I polymerases and its derivatives, T7 polymerases, an RB69 polymerase, T5 polymerases, or a polymerase corresponding to a Klenow fragment of a DNA Pol I polymerase, as well as other polymerases that share homologous sequences and/or active site structures. For example, the recombinant DNA polymerase can be homologous to a wild-type or exonuclease deficient Φ29 DNA polymerase, e.g., as described in U.S. Pat. Nos. 5,001,050, 5,198,543, or 5,576,204. Similarly, DNA polymerases can be homologous to Φ29, B103, GA-1, PZA, Φ15, BS32, M2Y, Nf, G1, Cp-1. PRD1, PZE, SF5, Cp-5, Cp-7, PR4, PR5, PR722, or L17, or the like.

As noted above, the reaction compositions of the invention will also typically include additional components for optimizing reaction conditions, including, e.g., buffers, salts, divalent metal ions, e.g., $Mg^{++}$ and/or $Mn^{++}$.

III. Methods

The compositions of the invention are particularly suited to analytical applications employing polymerase mediated nucleic acid synthesis, including, for example, real time nucleic acid amplification processes and nucleic acid sequencing by incorporation processes. Examples of nucleic acid sequence by incorporation processes are described, for example in U.S. Pat. No. 6,210,891, which describes a sequencing process in which incorporation is detected through the enzymatic identification of pyrophosphate released from an incorporated nucleotide. As will be appreciated, the compounds of the invention would provide a facile mechanism for the fluorescent detection of released pyrophosphate, based upon the labeling moieties used for the nucleotide analogs. More preferred methods employ the real time identification of incorporation events, including identification of the type of nucleotide analog incorporated (i.e., A, C, G, or T), as described above.

In the context of the invention, the compounds of the invention are provided to the complex that comprises a complementary polymerase enzyme (as described above) for the given analog structures. Upon incorporation, the polymerase retains the nucleotide analog in its active site, giving rise to a fluorescent signal associated with incorporation, e.g., based upon enhanced retention time within an illumination volume, generation of an unquenched fluorescent group, bringing a complementary FRET pair into sufficient proximity, or the like. The nature of the fluorescent signal is indicative of both incorporation, and the type of nucleotide incorporated. The fluorescent signals are detected and evaluated in order to give rise to a called base in the overall sequence of the template (See, e.g., U.S. Patent Application No. 60/933,399, the full disclosure of which is incorporated herein by reference in its entirety for all purposes).

IV. Systems

The systems of the invention typically employ those types of fluorescent detection schemes described in, e.g., Published U.S. Patent Application No. 2007/0188750, and copending U.S. patent application Ser. No. 11/901,273, filed Sep. 14, 2007, the full disclosures of which are incorporated herein by reference, in conjunction with the compositions described herein.

Figure 11:
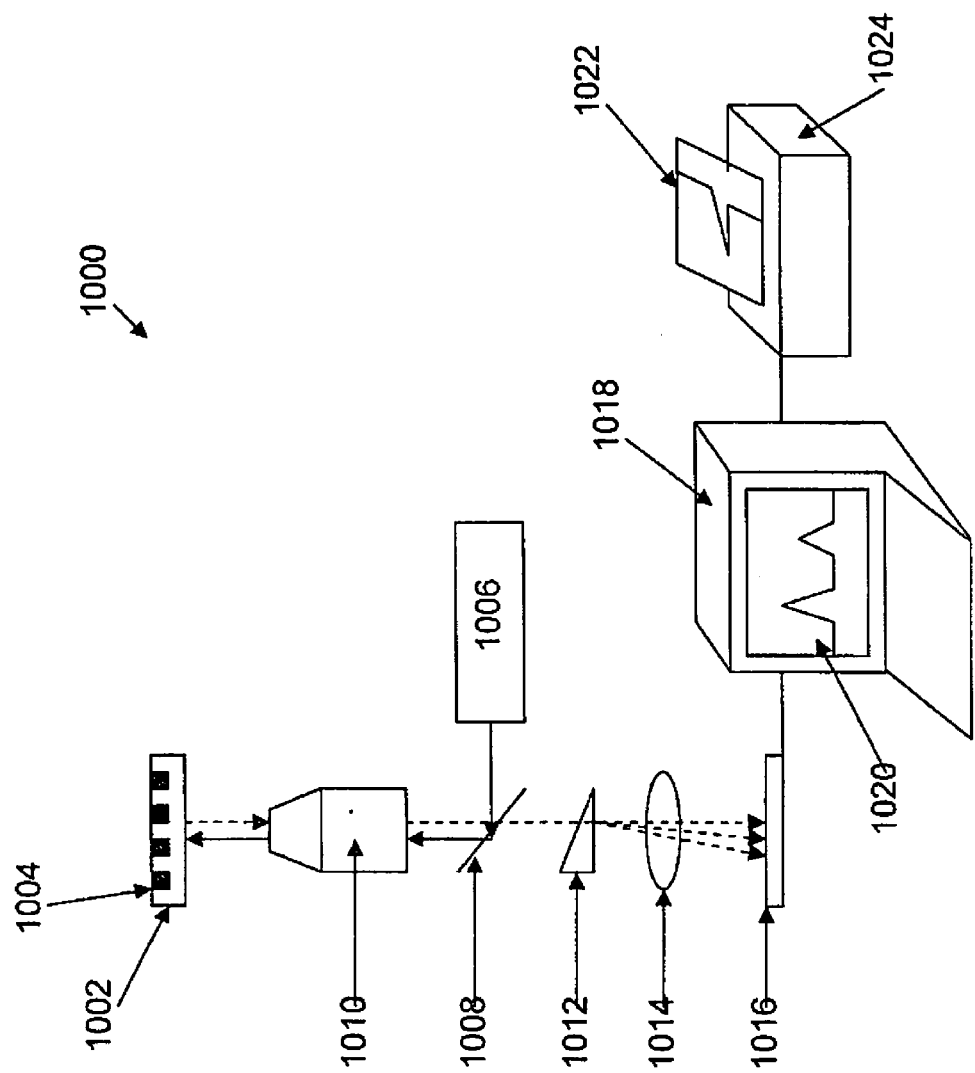
FIG. 11 schematically illustrates an exemplary system used in observing sequencing reactions.

One exemplary system is shown in FIG. 11. As shown, the system 1000 includes a substrate 1002 that includes a plurality of discrete reaction regions, e.g., reaction wells or optical confinements 1004 containing immobilized polymerase/template/primer complexes. An excitation light source, e.g., laser 1006, is optionally provided in the system and is positioned to direct excitation radiation at the various reaction regions 1004. This is typically done by directing excitation radiation at or through appropriate optical components, e.g., dichroic 1008 and objective lens 1010, that direct the excitation radiation at the substrate 1002, and particularly the reaction regions 1004. Emitted fluorescence from the reactions, e.g., from incorporating nucleotides, in reaction regions 1004 are then collected by the optical components, e.g., objective 1010, and passed through additional optical elements, e.g., dichroic 1008, prism 1012 and lens 1014, until they are directed to and impinge upon an optical detection system, e.g., detector array 1016. The signals are then detected by detector array 1016, and the data from that detection is transmitted to an appropriate data processing unit, e.g., computer 1018, where the data is subjected to interpretation, analysis, and ultimately presented in a user ready format, e.g., on display 1020, or printout 1022, from printer 1024.

V. Kits

The compositions of the invention are also typically provided in kit format along with other useful components. For example, such other kit components will typically include, in addition to the nucleotide compositions described herein, appropriate buffers, salts and the like, as described above, as well as complementary polymerase enzymes, and optionally primer sequences for the desired application. Such primers may be specific to the identification of a known genetic sequence, e.g., identifying specific genetic sequences, such as those associated with certain pathologies, e.g., viral infections, bacterial infections, cancer cell types, and the like. Alternatively, for non-targeted sequencing applications, universal primer sequences may be included.

In the case of applications that employ specific detection strategies, e.g., TIRF based detection or ZMW based detection, the kits may also include appropriate substrates for carrying out the analysis. For example, the kits may employ a zero mode waveguide array within the kit that may be pretreated to already include or be ready for immobilization

VI. Examples

Analogs that included hydrophobic polymerase interacting components were tested as substrates for four polymerase variants, each having a tyrosine residues at the 375 and 512 positions, and compared against other analogs that did not include hydrophobic polymerase interacting components. The analogs tested were Alexa 680-Hex-O-dA6P, Alexa 660-Hex-O-dA6P, Alexa 568-Hex-O-dT6P, Alexa 568-Hept-Hex-O-dT6P, Alexa 680-Hex-O-dG6P, Alexa 647-Hex-O-dG6P, Alexa 555-Hept-Hex-dC 6P, Alexa 488-Hept-Hex-O-dC6P, Cy3B-Hept-Hex-O-dC6P, Anthr-Hex-Hex-O-dA6P, Alexa 555-Hex-O-dG6P, Naph-Hex-Hex-O-dA6P, Alexa 647-Hex-O-dA6P, Alexa 488-Hept-Hex-O-dA6P, Alexa 488-Hex-O-dC6P, where "Hex" denotes a aminohexyl linker and "Hept-Hex" denotes a aminohexyl heptanoic acid linker.

Figure 12:
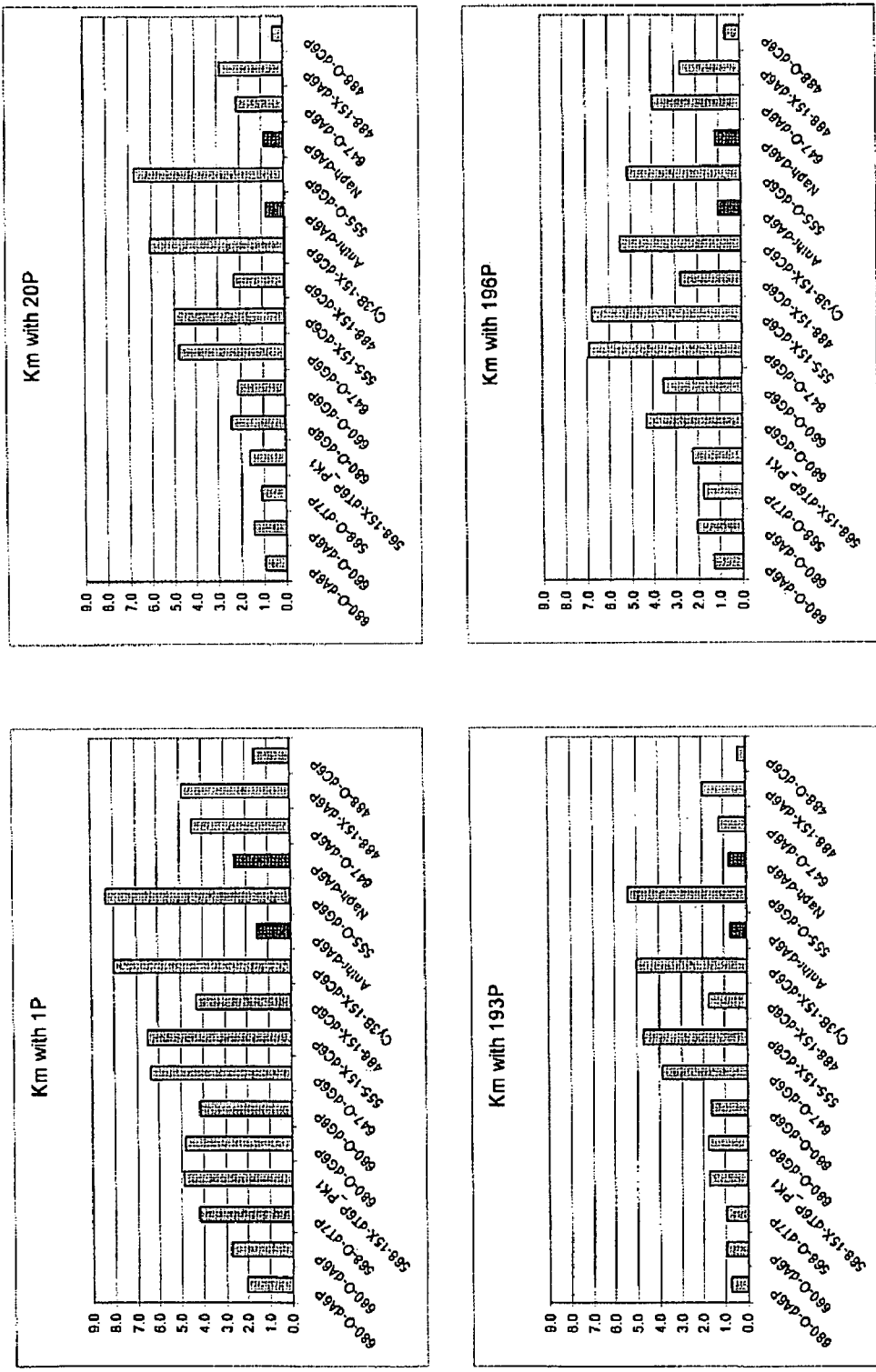
FIG. 12 shows a set of comparative plots of compounds of the invention tested against different polymerase variants.

The Km was determined for each enzyme analog combination and the results were plotted as the bar graphs shown in FIG. 12. The Hept-Hex linkers are denoted by the "15×" notation in the figure, while the other compounds included an amino hexyl linker. As can be seen, both the compound that included the Napthyl and anthracyl polymerase interacting components showed improved kinetics in the form of lower Km values against each of the four enzyme variants.

Although described in some detail for purposes of illustration, it will be readily appreciated that a number of variations known or appreciated by those of skill in the art may be practiced within the scope of present invention. All terms used herein are intended to have their ordinary meaning unless an alternative definition is expressly provided or is clear from the context used therein. For methods recited herein, to the extent that a composition of the invention is disclosed as being provided in a method step, it will be appreciated that disclosure of such provision implicitly discloses the preparation of such composition in a transformative fashion. To the extent any definition is expressly stated in a patent or publication that is incorporated herein by reference, such definition is expressly disclaimed to the extent that it is in conflict with the ordinary meaning of such terms, unless such definition is specifically and expressly incorporated herein, or it is clear from the context that such definition was intended herein. Unless otherwise clear from the context or expressly stated, any concentration values provided herein are generally given in terms of admixture values or percentages without regard to any conversion that occurs upon or following addition of the particular component of the mixture. To the extent not already expressly incorporated herein, all published references and patent documents referred to in this disclosure are incorporated herein by reference in their entirety for all purposes.

What is claimed is:

1. A nucleotide composition, comprising the structure:

wherein N is a nucleoside polyphosphate or analog thereof; F is a detectable label moiety; and
Y comprises a polymerase interacting linkage complex comprising a polymerase interacting group positioned from 20 to 40 angstroms from a nucleoside portion of the nucleoside polyphosphate.

2. The nucleotide composition of claim 1, wherein the polymerase interacting linkage complex (Y) comprises the structure:

where $L_1$ is a first linker group, P is a polymerase interacting group, and $L_2$ is a second linker group.

3. The nucleotide composition of claim 1, wherein the polymerase interacting linkage complex (Y) comprises the structure:

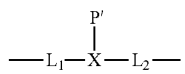

where $L_1$ is a first linker group, P' is a polymerase interacting group, $L_2$ is a second linker group, and X is a linking group.

4. The nucleotide composition of claim 3, wherein the polymerase interacting component comprises a hydrophobic group having one or more phenyl groups.

5. The nucleotide composition of claim 4, wherein the polymerase interacting component comprises a hydrophobic group comprising a phenyl group, a biphenyl group, a triphenyl group and a coumarin or coumarin derivative group.

6. The nucleotide composition of claim 2, comprising a structure selected from:

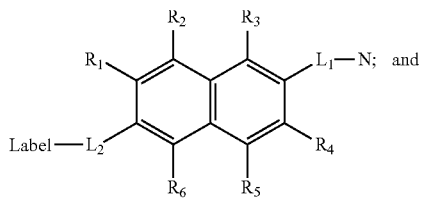

-continued

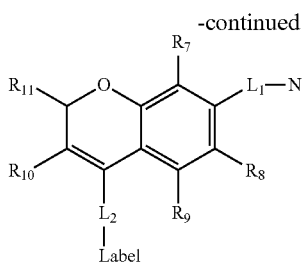

where $R_1$ through $R_{11}$ are independently selected from H, O, OH, positively charge groups and negatively charged groups.

7. The nucleotide composition of claim 6, wherein $R_1$ through $R_{11}$ are independently selected from oxygen, hydroxyl, guanidinium, amine, ammonium, iminium, oxonium, carboxyl, phosphate, phosphonate, thio, sulfate, sulfonate, thioate, and phosphothioate groups.

8. The nucleotide composition of claim 6, wherein $R_{11}$ comprises a group selected from $SO_3$, $PO_3$, OH, or a double bonded O.

9. A nucleotide composition, comprising the structure:

N—Y—F where N is a nucleoside polyphosphate group or analog thereof coupled through a phosphate group other than an alpha phosphate group;

L is a detectable labeling group; and

Y comprises a polymerase interacting linkage complex having a polymerase interacting component selected from phenyl, biphenyl, triphenyl and a coumarin derivative positioned from 20 to 40 angstroms from a nucleoside portion of the nucleoside polyphosphate.

10. The composition of claim 9, wherein N comprises a naturally occurring nucleoside coupled to a polyphosphate group.

* * * * *

UNITED STATES PATENT AND TRADEMARK OFFICE
CERTIFICATE OF CORRECTION

| | |
|---|---|
| PATENT NO. | : 7,973,146 B2 |
| APPLICATION NO. | : 12/412068 |
| DATED | : July 5, 2011 |
| INVENTOR(S) | : Gene Shen, Paul Peluso and Arkadusz Bibillo |

It is certified that error appears in the above-identified patent and that said Letters Patent is hereby corrected as shown below:

Column 2, line 44, please replace the designation "L" with the correct designation --F--. The corrected line 44 will read --alpha phosphate group, F is a detectable labeling group, and--.

In the Claims, column 20, line 10, please replace the designation "L" with the correct designation --F--. The corrected line 10 will read --F is a detectable labeling group; and--.

Signed and Sealed this
Fifteenth Day of November, 2011

David J. Kappos
*Director of the United States Patent and Trademark Office*